United States Patent
Ouchi

[11] Patent Number: 6,086,583
[45] Date of Patent: Jul. 11, 2000

[54] ELECTRIC CAUTERY FOR ENDOSCOPE

[75] Inventor: Teruo Ouchi, Saitama-ken, Japan

[73] Assignee: Asahi Kogaku Kogyo Kabushiki Kaisha, Tokyo, Japan

[21] Appl. No.: 09/088,706

[22] Filed: Jun. 2, 1998

[30] Foreign Application Priority Data

| Jun. 5, 1997 | [JP] | Japan | 9-147756 |
| Jun. 5, 1997 | [JP] | Japan | 9-147757 |
| Jun. 5, 1997 | [JP] | Japan | 9-147758 |
| Jun. 20, 1997 | [JP] | Japan | 9-163580 |

[51] Int. Cl.[7] .................................... A61B 18/18
[52] U.S. Cl. ................ 606/41; 606/46; 606/48; 606/50; 604/35
[58] Field of Search .............. 606/41–50; 604/35

[56] References Cited

U.S. PATENT DOCUMENTS

| 4,311,144 | 1/1982 | Harada . | |
| 5,084,045 | 1/1992 | Helenowski | 606/49 |
| 5,133,714 | 7/1992 | Beane | 606/49 |
| 5,277,696 | 1/1994 | Hagen | 606/49 |
| 5,697,882 | 12/1997 | Eggers et al. | 604/114 |
| 5,730,742 | 3/1998 | Wojciechowicz | 606/49 |
| 5,814,044 | 9/1998 | Hooven | 606/48 |
| 5,904,681 | 5/1999 | West, Jr. | 606/41 |
| 5,906,615 | 5/1999 | Thompson | 606/45 |

FOREIGN PATENT DOCUMENTS

| 60-31688 | 9/1985 | Japan . |
| 61-7696 | 3/1986 | Japan . |
| 8131397 | 5/1996 | Japan . |

Primary Examiner—Linda C. M. Dvorak
Assistant Examiner—David M. Ruddy
Attorney, Agent, or Firm—Greenblum & Bernstein, P.L.C.

[57] ABSTRACT

An electric cautery used with an endoscope includes a hood mounted to a distal end of an insertion part of the endoscope. An electrode is provided to an inner surface and/or an end surface of the hood. A cable is provided to supply electricity to the electrode. The cable extends in the channel of the insertion part of the endoscope.

16 Claims, 34 Drawing Sheets

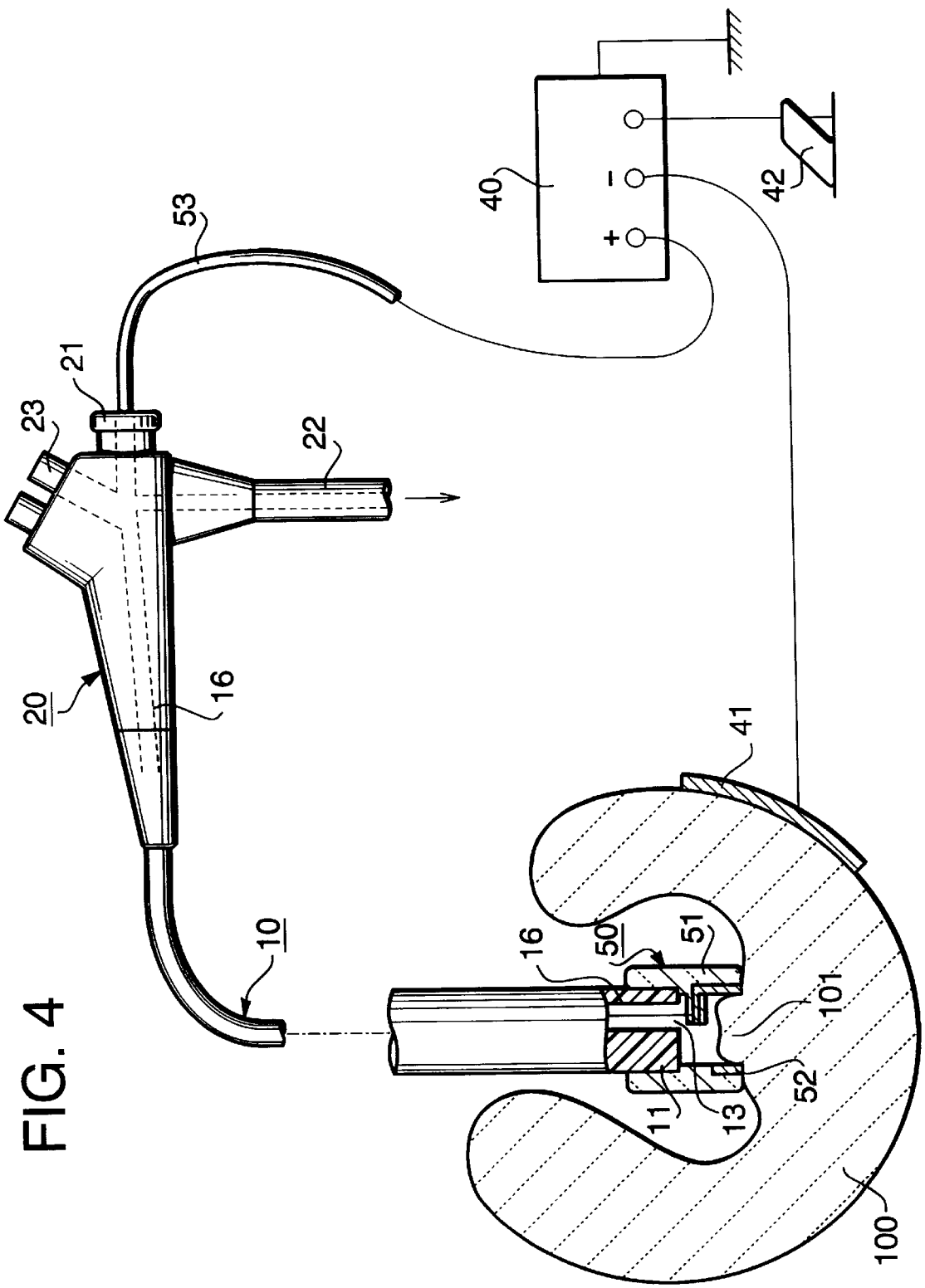

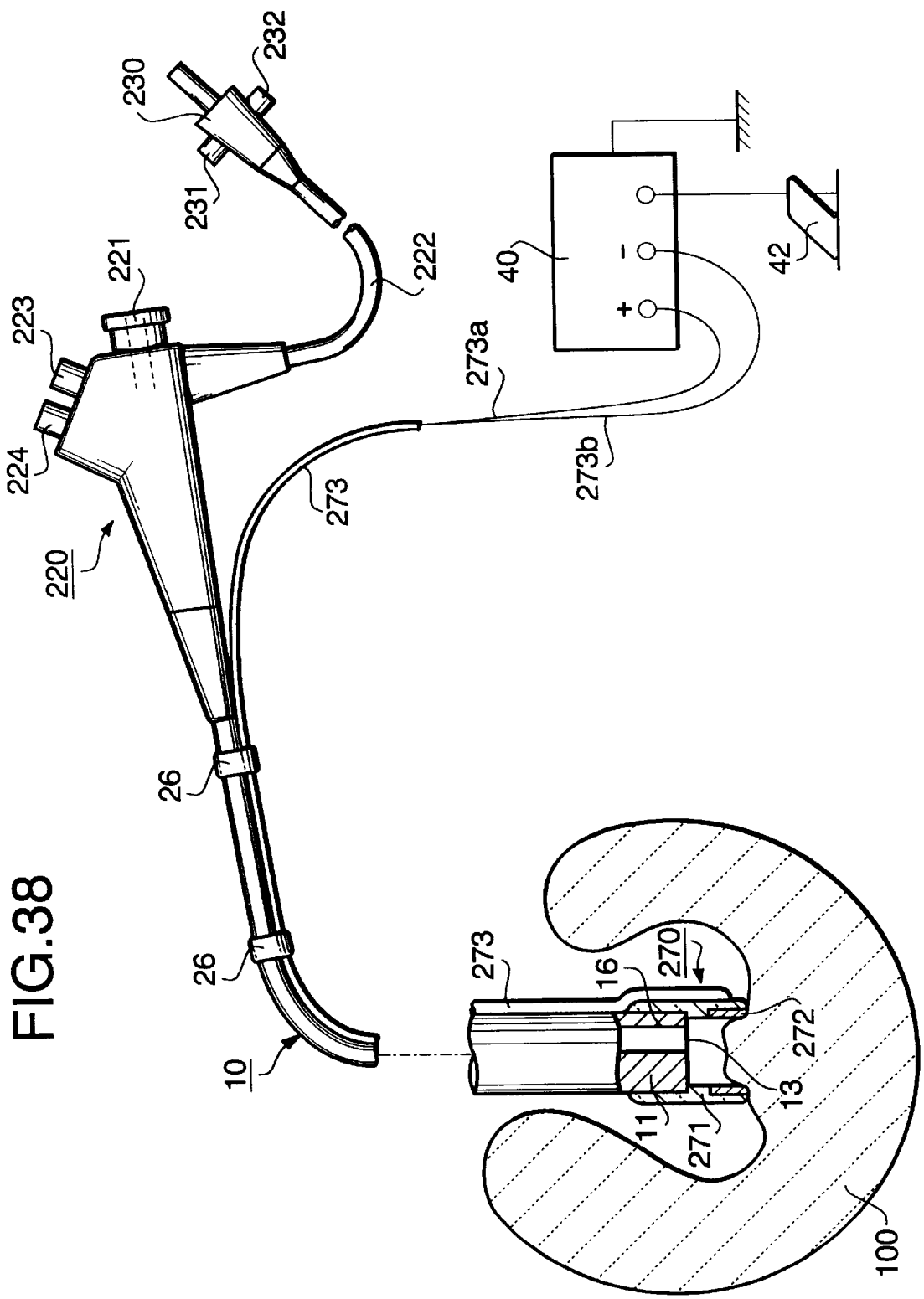

ELECTRIC CAUTERY FOR ENDOSCOPE

BACKGROUND OF THE INVENTION

The present invention relates to an electric cautery used with an endoscope.

In an endoscopic surgery, the electric cautery is used to stop bleeding after treatment or the like. A conventional electric cautery includes a probe that is inserted into a human body cavity through a channel of an endoscope. An operator urges the probe to a surface of the human body cavity, and then applies a high-frequency voltage to the prove thereby to heat the surface of the human body cavity.

However, since the probe is inserted through the channel of the endoscope, the probe should be smaller than the inner diameter of the channel. Thus, it is not possible to cauterize a large area at a time.

In order to cauterize a large area at a time, another type of electric cautery is developed. The electric cautery of this type has a balloon and a microwave generator provided in the balloon. Initially, the balloon is shrunk so that the balloon can be inserted into the human body cavity through the endoscope. After the balloon is inserted into the human body cavity, the operator expands the balloon so that an outer surface of the balloon abuts the surface of the human body cavity, and then turns on the microwave generator so that microwaves irradiate the surface of the human body cavity. However, in such a balloon-type electric cautery, an operation of expanding the balloon is complicated.

Accordingly, an electric cautery capable of cauterizing a large area and which can be operated in a simple manner is desired.

There is still another type of electric cautery used to cauterize a relatively small area. The electric cautery of this type includes a biopsy forceps. The biopsy forceps has a pair of cups which grip the surface of the human body cavity therebetween. An operator manipulates the biopsy forceps to grip the surface of the human body cavity, and then applies a high-frequency voltage to the biopsy forceps to cauterize the surface gripped by the biopsy forceps. However, in such an electric cautery, an operation for accurately griping a surface of the human body cavity with the biopsy forceps is not easy.

Accordingly, an electric cautery for cauterizing a small area which can be operated in a simple manner is desired.

SUMMARY OF THE INVENTION

It is therefore a first object of the present invention to provide to an electric cautery capable of cauterizing a large area and which can be operated in a simple manner.

According to an aspect of the present invention, there is provided an electric cautery including a hood mounted to a distal end of an insertion part of the endoscope. At least one electrode is provided to an inner surface and/or an end surface of the hood. At least one cable extends in the channel, for supplying electricity to the electrode. The endoscope includes an elongated insertion part to be inserted into a human body cavity. The insertion part has at least one channel that opens at a distal end of the insertion part. The channel enables the suction via an opening formed on the distal end of the insertion part.

With such an arrangement, since the electrode is provided to an inner surface and/or an end surface of the hood, it is possible to cauterize a large area at a time. Further, when the suction is operated, a surface of the human body cavity is sucked in the hood. Thus, the surface of the human body cavity sufficiently contacts the electrode. This enables efficient cauterizing.

Preferably, the hood is detachably mounted to a periphery of the distal end of the insertion part. Thus, when the hood is detached from the insertion part, the endoscope can be used for other purposes. Optionally, an inner surface of the electrode is inwardly projected from an inner surface of the hood. With this, the electrode is urged to the surface of the human body cavity, so that the electrode sufficiently contacts the surface of the human body cavity.

In a particular arrangement, the electric cautery includes a contact plate which contacts a human body. In such case, voltages of reversed polarity are applied to the electrode and the contact plate. In another particular arrangement, the electric cautery includes at least one pair of electrodes. In such case, voltages of reversed polarity are applied to the pair of electrodes.

Conveniently, the hood includes a protrusion which inwardly protrudes from an inner surface of the hood. The cable and the electrode are electrically connected with each other in the protrusion. Further, the opening of the channel and the protrusion are overlapped with each other in a direction of axis of the insertion part. Thus, the cable and the electrode can be connected in a simple manner. Furthermore, a gap is provided between the protrusion and the opening of the channel. With this, the protrusion does not interfere with the suction via the opening of the channel.

According to another aspect of the present invention, there is provided an electric cautery including a hood mounted to the distal end of the insertion part of the endoscope. At least one electrode is provided to an outer surface of the hood. At least one cable (for supplying electricity to the electrode) extends in the channel formed in the insertion part of the endoscope.

With such an arrangement, since the electrode is provided to an outer surface of the hood, it is possible to cauterize a large area at a time. Further, when the suction is operated, the human body cavity is contracted so that the surface thereof sufficiently contacts the electrode. This enables efficient cauterizing.

Preferably, the electrode extends in a circumferential direction of the hood, thereby to further increase the area to be cauterized. Alternatively, the electrode includes a plurality of electrodes, each of which extends in an axial direction of the hood. With this, it is possible to cut a isthmus or the like by the electrode.

According to still another aspect of the present invention, there is provided an electric cautery including a hood mounted to the distal end of the insertion part of the endoscope. At least one electrode is provided to an inner surface and/or an end surface of the hood. At least one cable is provided to a periphery of the insertion part of the endoscope, for supplying electricity to the electrode.

With such an arrangement, since the cable does not exist in the channel, the channel can be used for inserting another instrument such as a forceps, a snare or the like. Thus, it is possible to use the electric cautery and other instrument at the same time.

It is a second object of the present invention to provide an electric cautery for cauterizing a small area which can be operated in a simple manner.

According to further aspect of the present invention, there is provided an electric cautery including a tube inserted through the channel of the insertion part, at least one electrode provided to a tip of the tube, at least one cable extending in the tube for supplying electricity to the electrode.

With such an arrangement, by urging the tip of the tube to the surface of the human body cavity, it is possible to surely cauterize a small area of the surface of the human body cavity. Further, when the suction is operated, a surface of the human body cavity is sucked in the tube so that the electrode sufficiently contacts the surface of the human body cavity. This enables efficient cauterizing.

In a particular arrangement, the electrode is embedded in a sheath of the tube. It is alternatively possible that the electrode extends in a hollow portion of the tube. Optionally, it is possible to provide the electrode to an inner surface of the tip of the tube. Furthermore, it is preferable that the electrode includes a plurality of pins located in a hollow portion of the tube.

BRIEF DESCRIPTION OF THE DRAWINGS

FIG. 4 is a sectional view showing the operating electric cautery of FIG. 1;

FIG. 38 is a schematic view illustrating a system for operating the electric cautery of FIG. 37;

DESCRIPTION OF THE PREFERRED EMBODIMENT

[First Embodiment]

Figure 1:
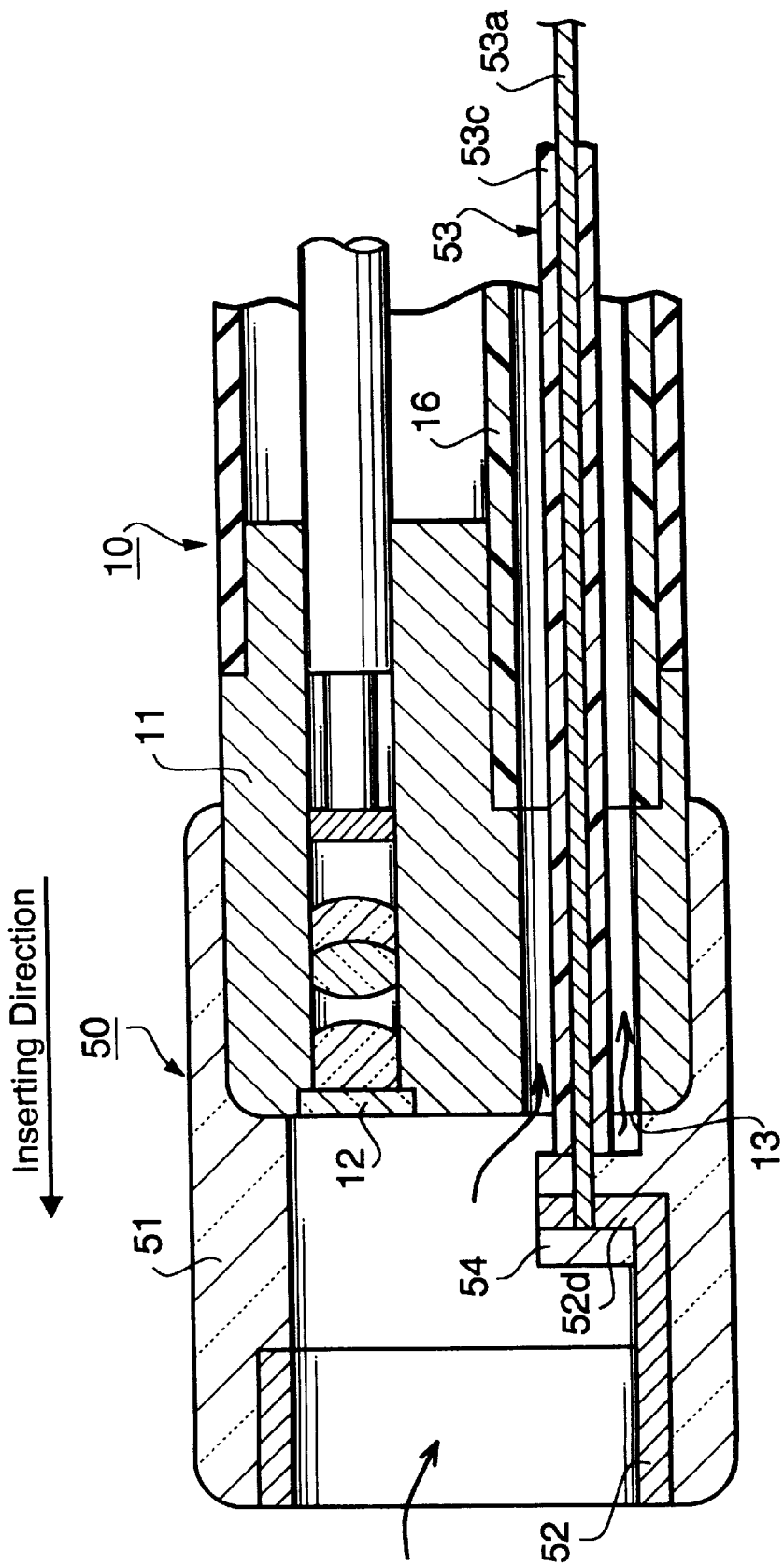
FIG. 1 is a sectional view showing an electric cautery of the first embodiment.

The first embodiment of the present invention is described. FIG. 1 is a sectional view showing an electric cautery 50 of the first embodiment (mounted to an insertion part 10 of an endoscope). In FIG. 1, a head end of the insertion part 10 in the inserting direction is defined as a "distal end". On the other hand, a tail end of the insertion part 10 which is connected to an operation part 20 (FIG. 4) is defined as a "proximal end".

Figure 2:
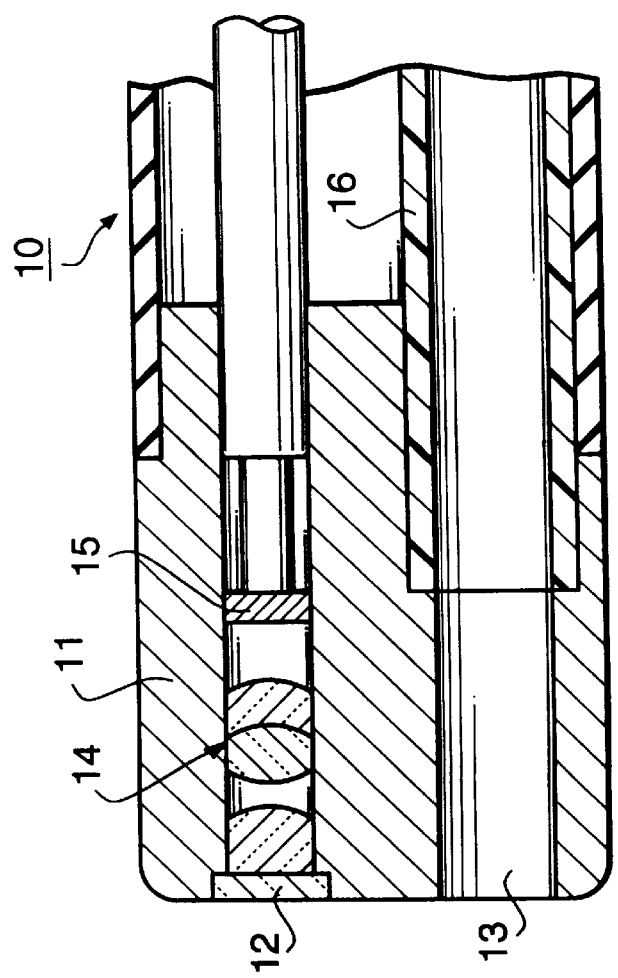
FIG. 2 is a sectional view showing an insertion part.

FIG. 2 is a sectional view showing a distal end portion 11 of the insertion part 10. As shown in FIG. 2, a view window 12, a suction opening 13 and an illumination window 12a (FIG. 3) are provided at an end surface of the distal end portion 11. An object lens group 14 is provided behind the view window 12, which forms an image taken through the view window 12. Further, a CCD 15 is located at an image plane of the object lens group 14. The CCD 15 can be replaced with an image-guide fiber. The suction opening 13 leads to a suction channel 16 extending in the insertion part 10.

As shown in FIG. 1, the electric cautery 50 includes a cylindrical hood 51 mounted to the distal end portion 11. The distal end portion 11 has a circle cross section, and is fit into the hood 51. The hood 51 can be detached from the distal end portion 11 of the insertion part 10. Thus, when the electric cautery 50 is not in use, the endoscope can be used for other purpose. It is alternatively possible to provide threads on the hood 51 and the distal end portion 11 so that the hood 51 is mounted to the distal end portion 11 by thread engagement. The hood 51 is made of insulating plastic which is transparent. Since the hood 51 is transparent, an operator can observe a surface of the human body cavity through the view window 12 without interference by the hood 51.

An electrode 52 is provided to the inner surface of the hood 51. In order to supply electricity to the electrode 52, a cable 53 is connected to the electrode 52. The cable 53 is extended through the suction channel 16 to a power source 40 (FIG. 4). The cable 53 includes a lead wire 53a and a sheath 53c formed around the lead wire 53a.

Figure 3:
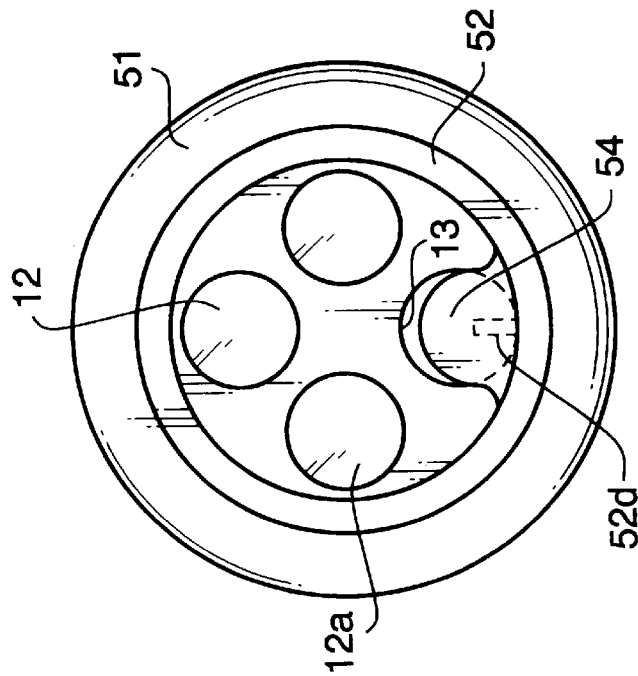
FIG. 3 is a front view of the electric cautery of FIG. 1.

FIG. 3 is a front view of the electric cautery 50 mounted to the insertion part. The electrode 52 extends throughout the inner circumference of the hood 51. A protrusion 54 is formed on a inner surface of the hood 51. The protrusion 54 is protruded inwardly so that the protrusion 54 is overlapped with the suction opening 13. A part 52d of the electrode 52 extends to the protrusion 54. As shown in FIG. 1, one end of the cable 53 is fixed to the protrusion 54. In the protrusion 54, the lead wire 53a is connected to the part 52d of the electrode 52. Since the outer diameter of the cable 53 is smaller than the inner diameter of the suction channel 16, suction is enabled through a gap around the cable 53 in the suction channel 16. Further, a gap is provided between the protrusion 54 and the suction opening 13 so that the protrusion 54 does not prevent the suction.

FIG. 4 is a schematic view illustrating a system for operating the electric cautery 50. The proximal end of the insertion part 10 is fixed to an operation part 20. The suction channel 16 extends through the operation part 20 and leads to an opening 21 provided at a rear end of the operation part 20. The cable 53 extends to the exterior of the operation part 20 through the opening 21. The lead wire 53a of the cable 53 is connected to plus terminal of the power source 40. A contact plate 41 is attached to the surface of the human body 100 and is connected to the minus terminal of the power source 40 via a lead wire. That is, voltages of reversed polarity are applied to the electrode 52 and the contact plate 41.

A connection channel 22 is branched from the suction channel 16, which is connected to a suction apparatus (not shown) provided to the exterior of the operation part 20. Further, the operation part 20 is provided with an operation bulb 23 for controlling the suction.

Figure 5:
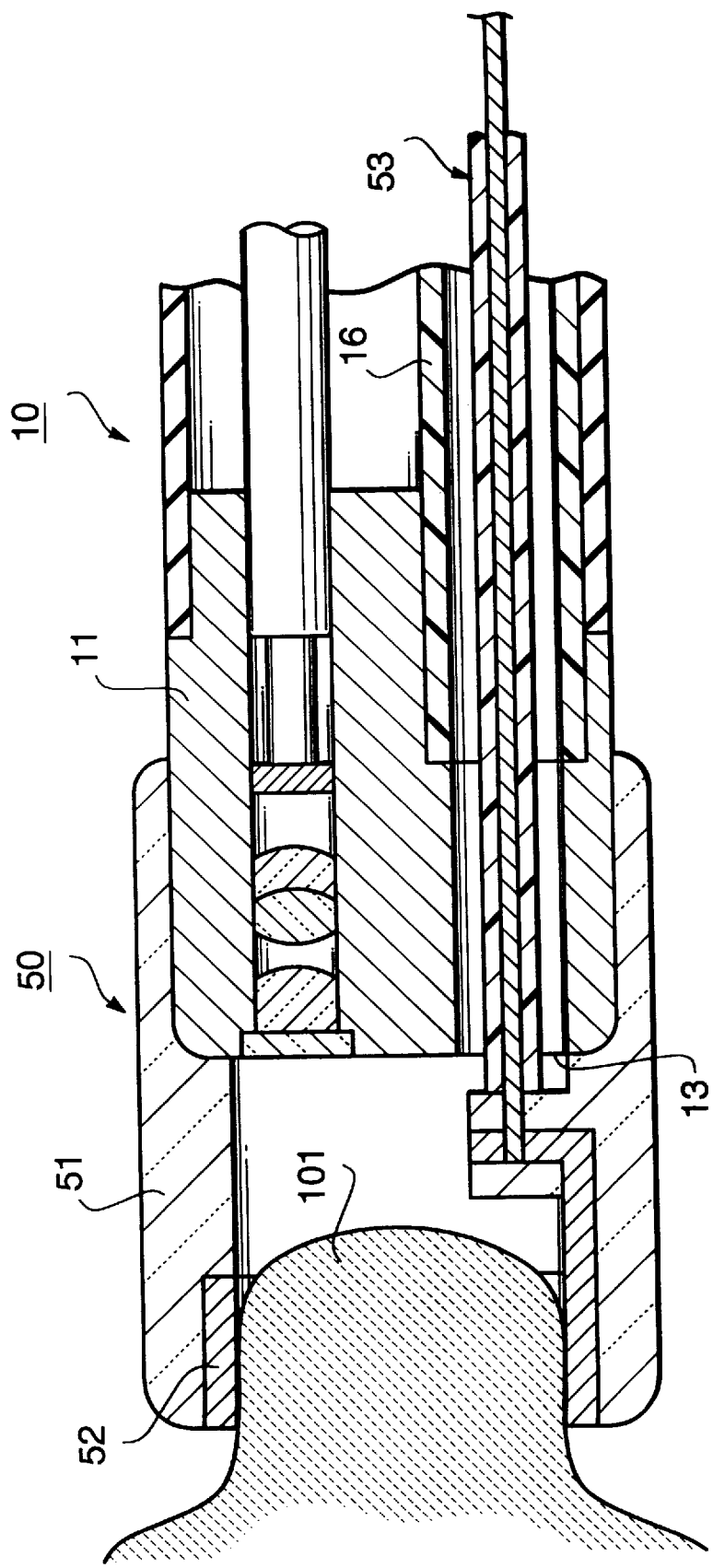
FIG. 5 is a schematic view illustrating a system for operating the electric cautery of FIG. 1.

The operation of the electric cautery is described. First, an operator manipulates the operation part 20 so that the hood 51 abuts the surface 101 of the human body cavity. Then, the operator turns the operation bulb 23 to start suction. With this, the surface 101 of the human body cavity is sucked in the hood 51 as shown in FIG. 5. Then, the operator presses a switch 42 of the power source 40 to apply high-frequency voltage to the electrode 52 and the contact plate 41, thereby to cauterize the surface 101 of the human body cavity.

Figure 6:
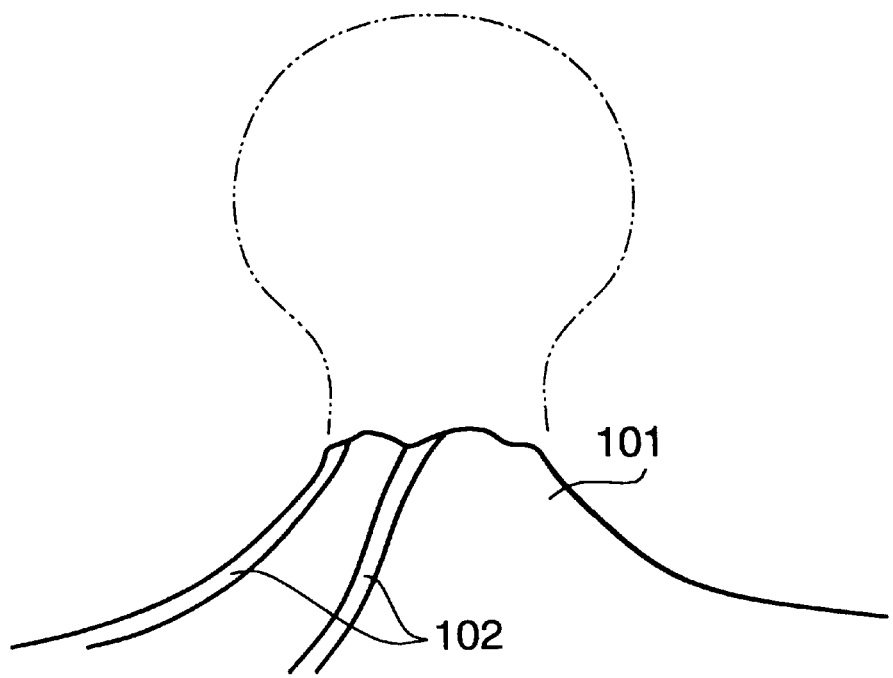
FIG. 6 is a schematic view of a surface of a human body cavity.
Figure 7:
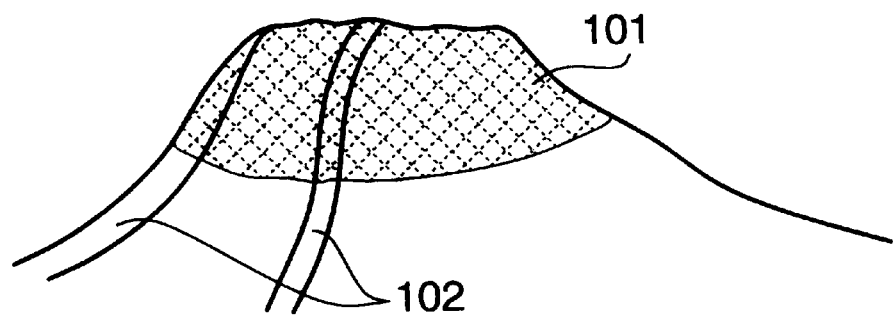
FIG. 7 is a schematic view of a surface of a human body cavity after cauterization.

As shown in FIG. 6, after a polyp (shown by dash-line) is removed, ends of blood lines 102 may be opened on the surface 101 of the human body cavity. However, according to the first embodiment, the surface 101 of the human body cavity is cauterized as shown by crosshatching in FIG. 7. Thus, the blood from the ends of blood lines 102 is clot. Further, the blood is partially sucked by the suction through the suction channel 16, when the inner surface 101 of the human body cavity is sucked in the hood 51.

As described above, according to the first embodiment, since the electrode 52 is formed on the inner surface of the hood 51, it is possible to cauterize a large area at a time. Further, since the surface 101 of the human body cavity is sucked in the hood 51, the surface 101 sufficiently contacts the electrode 52. This may enable efficient cauterizing.

Figure 8:
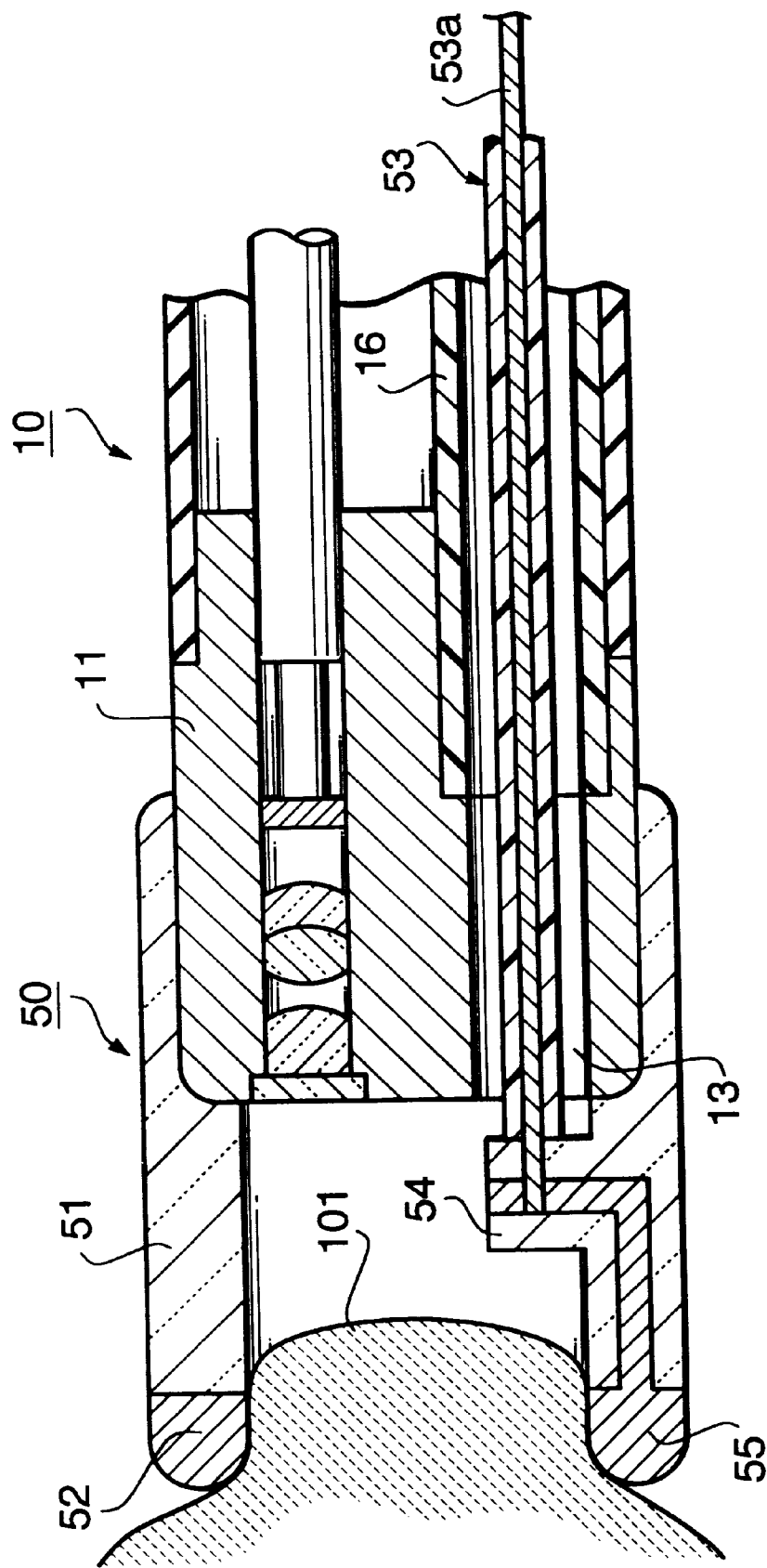
FIG. 8 is a sectional view showing an electric cautery of the modification of the first embodiment.

FIG. 8 is a sectional view showing the modification of the first embodiment. An electrode 55 of this modification is provided to the tip of the hood 51. The electrode 55 circumferentially extends along the tip of the hood 51. Further, the electrode 55 partially extends to the above-described protrusion 54, where the electrode 55 is electrically connected to the lead wire 53a. With such an arrangement, when the hood 51 abuts the surface 101 of the human body cavity, the electrode 55 deeply contacts the surface 101. This enables efficient cauterizing.

[Second Embodiment]

Figure 9:
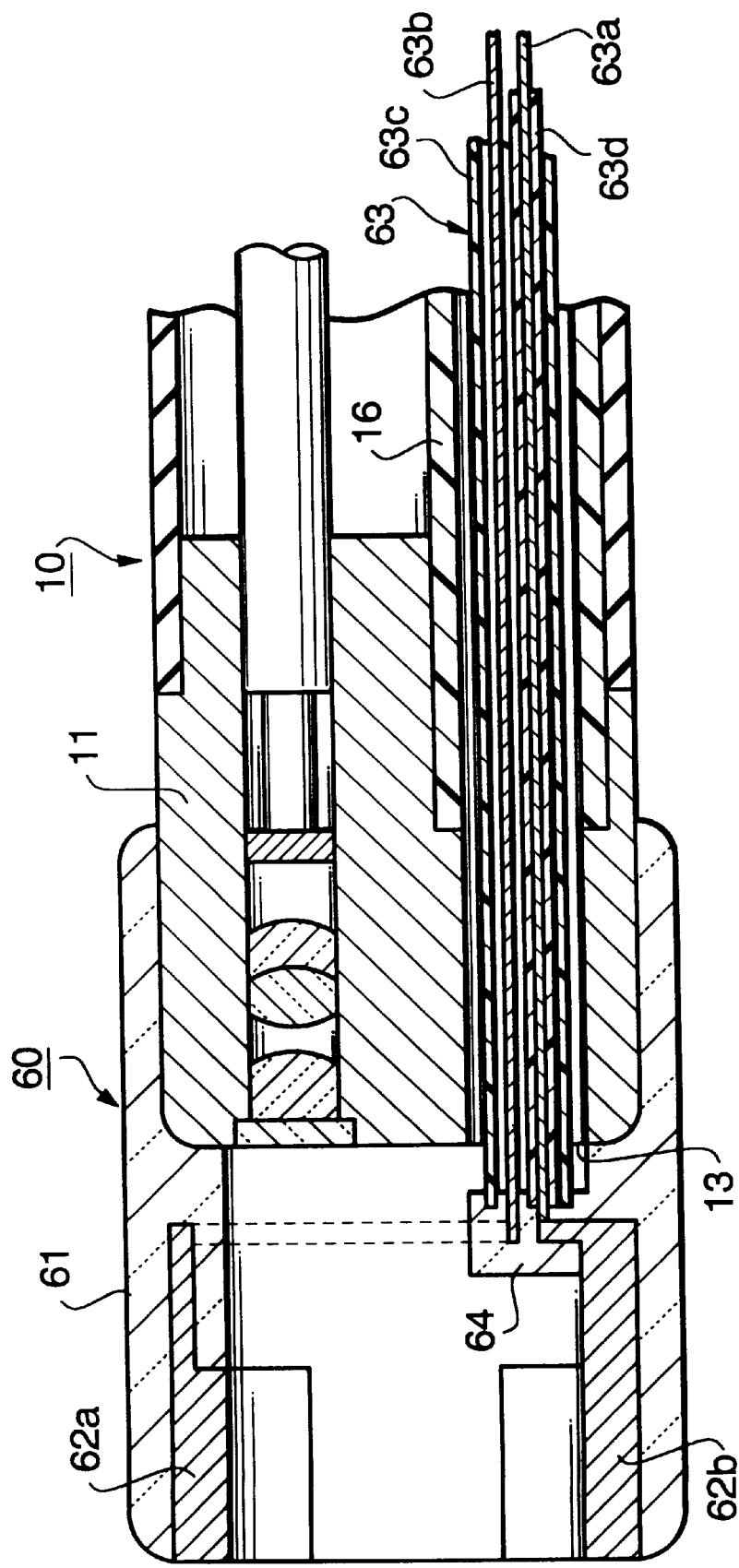
FIG. 9 is a sectional view showing an electric cautery of the second embodiment.
Figure 10:
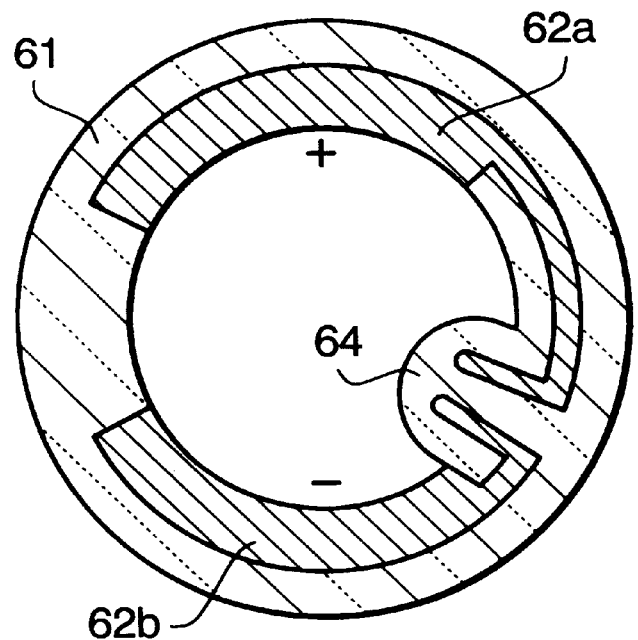
FIG. 10 is a sectional view of a hood of the electric cautery of FIG. 9.

The second embodiment of the present invention is described. FIG. 9 is a sectional view of an electric cautery 60 of the second embodiment (mounted to the insertion part). FIG. 10 is a front view of the electric cautery of FIG. 9. In the second embodiment, the structure of the insertion part 10 is the same as the first embodiment.

As shown in FIG. 9, the electric cautery 60 has a hood 61 mounted to the insertion part 10. The hood 61 is mounted to the distal end portion 11 of the insertion part 10 so that the distal end portion 11 is fit into the hood 61. The hood 61 can be detached from the distal end portion 11 of the insertion part 10. It is alternatively possible to provide threads on the hood 61 and the distal end portion 11 so that the hood 61 is mounted to the distal end portion 11 by thread engagement.

Figure 11:
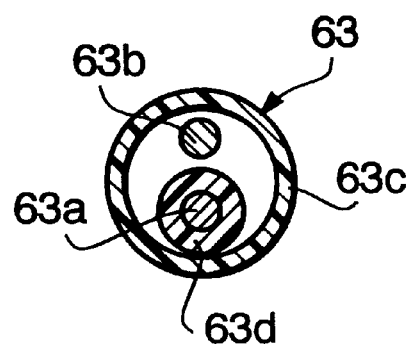
FIG. 11 is a sectional view of a cable of the electric cautery of FIG. 9.

As shown in FIG. 10, two electrode 62a and 62b are formed on the opposing side of the inner surface of the hood 61. The electrode 62a and 62b are extended to a protrusion 64 that projects inwardly from the inner surface of the hood 61. As shown in FIG. 9, a cable 63 is inserted through the channel 16 of the insertion part 10 and is fixed to the protrusion 64 of the hood 61. Lead wires 63a and 63b provided in the cable 63 extends in the protrusion 64, where the lead wires 63a and 63b are connected to the electrode 62a and 62b. As shown in FIG. 11, the lead wires 63a and 63b are supported in a sheath 63c made of an insulation material. In order to separate the lead wires 63a and 63b from each other, the lead wire 63a is covered by an insulation cover 63d.

The outer diameter of the cable 63 is smaller than the inner diameter of the suction channel 16. Further, there is a distance between the suction opening 13 and the protrusion 64 so that the protrusion 64 does not interfere with the suction. Thus, it is possible to perform suction through a suction opening 13.

Figure 12:
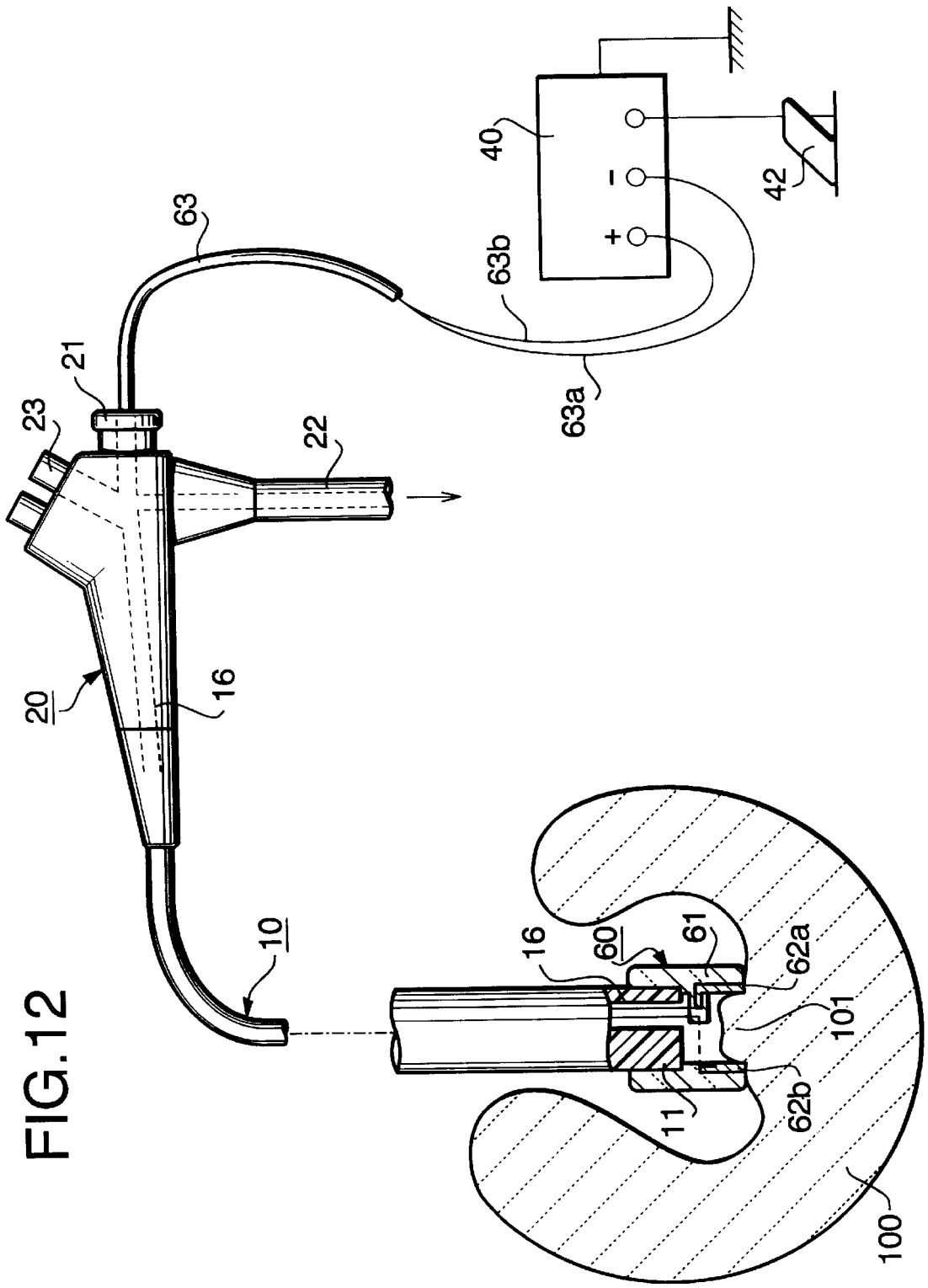
FIG. 12 is a schematic view of a system for operating the electric cautery of FIG. 9.

FIG. 12 is a schematic view illustrating a system for operating the electric cautery 60. The operation part 20 of the endoscope and the power source 40 are the same as those of the first embodiment. The lead wire 63a is connected to a plus terminal of the power source 40, while the lead wire 63b is connected to a minus terminal of the power source 40.

First, the operator manipulates the operation part 20 so that the hood 51 abuts the surface 101 of the human body cavity. Then, the operator starts the suction so that the surface 101 of the human body cavity is sucked in the hood 61. Then, the operator presses the switch 42 of the power source 40 to apply high-frequency voltage to the electrode 62a and 62b. With such an arrangement, the surface 101 of the human body cavity can be cauterized without providing a contact plate 41 (FIG. 4) of the first embodiment.

As described above, according to the second embodiment, it is possible to cauterize a large area of the surface of the human body cavity. Further, since plus and minus voltages are respectively applied to the electrodes 62a and 62b, it is not necessary to provide a contact plate 41 (of the first embodiment). That is, the structure of the electric cautery can be remarkably simple.

Figure 13:
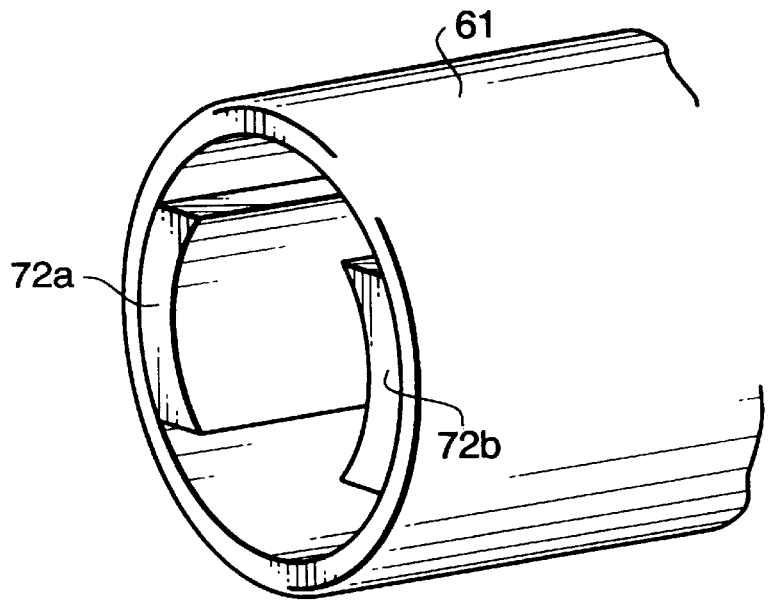
FIG. 13 is a perspective view of the electric cautery of the first modification of the second embodiment.

FIG. 13 shows a first modification of the second embodiment. Electrodes 72a and 72b of this modification project inwardly from the inner surface of the hood 61. With this, the electrodes 72a and 72b can tightly contact the surface of the human body cavity.

Figure 14:
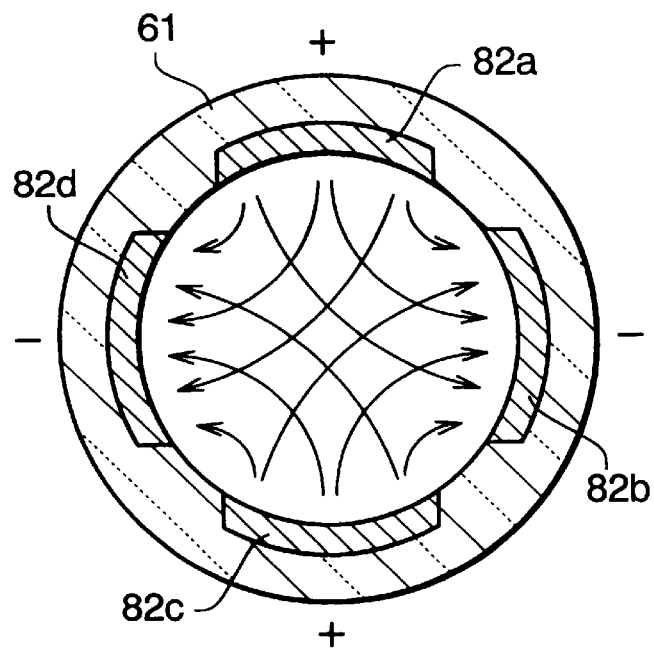
FIG. 14 is a front view of the electric cautery of the second modification of the second embodiment.

FIG. 14 shows a second modification of the second embodiment. In this modification, two pairs of electrodes 82a, 82b, 82c and 82d are provided to the inner surface of the hood 61. Plus voltage is applied to two opposing electrodes 82a and 82c, while minus voltage is applied to two opposing electrodes 82b and 82d. This arrangement generates current flows shown by arrows in FIG. 14. That is, the surface of the human body cavity can be uniformly heated. In this modification, it is also possible to increase the number of electrodes.

Figure 15:
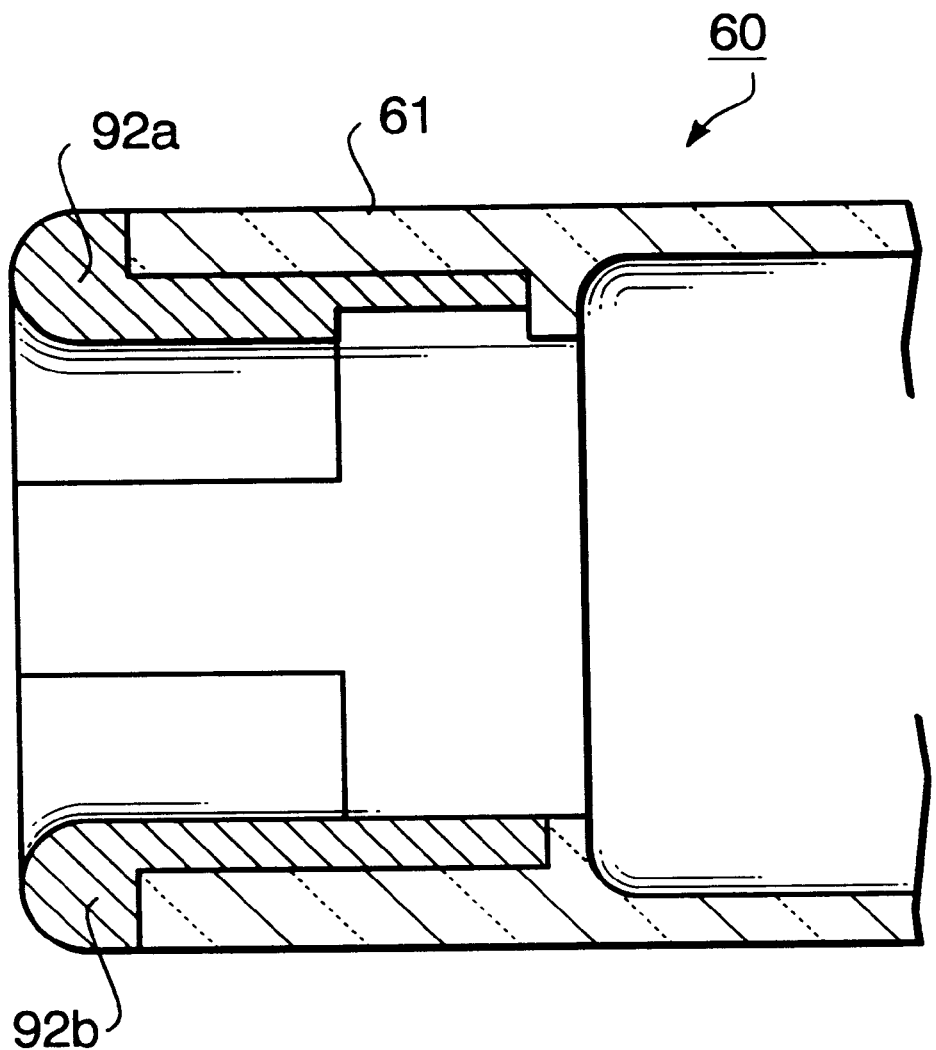
FIG. 15 is a sectional view of the electric cautery of the third modification of the second embodiment.

FIG. 15 shows a third modification of the second embodiment. Electrodes 92a and 92b of this modification are provided to the tip of the hood 61 as well as the inner surface of the hood 61. With this, the electrodes 92a and 92b contact the inner surface of the human body cavity in a larger area. That is, it is possible to cauterize a larger area at a time.

[Third Embodiment]

Figure 17:
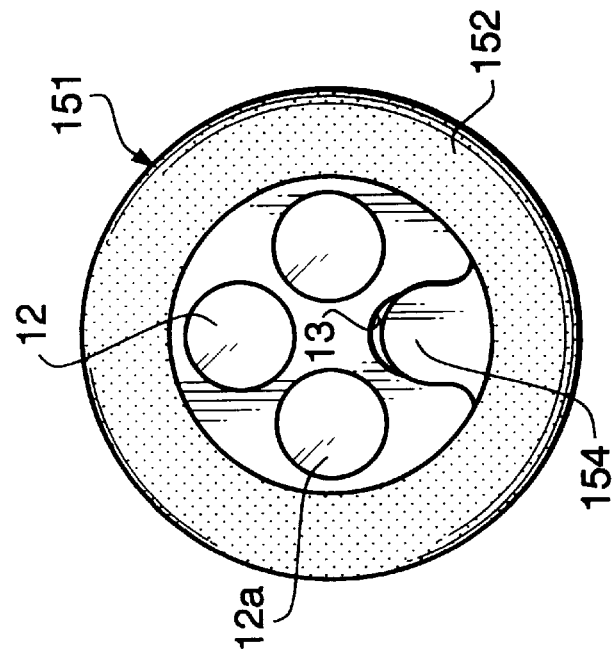
FIG. 17 is a front view of the electric cautery of FIG. 16.
Figure 16:
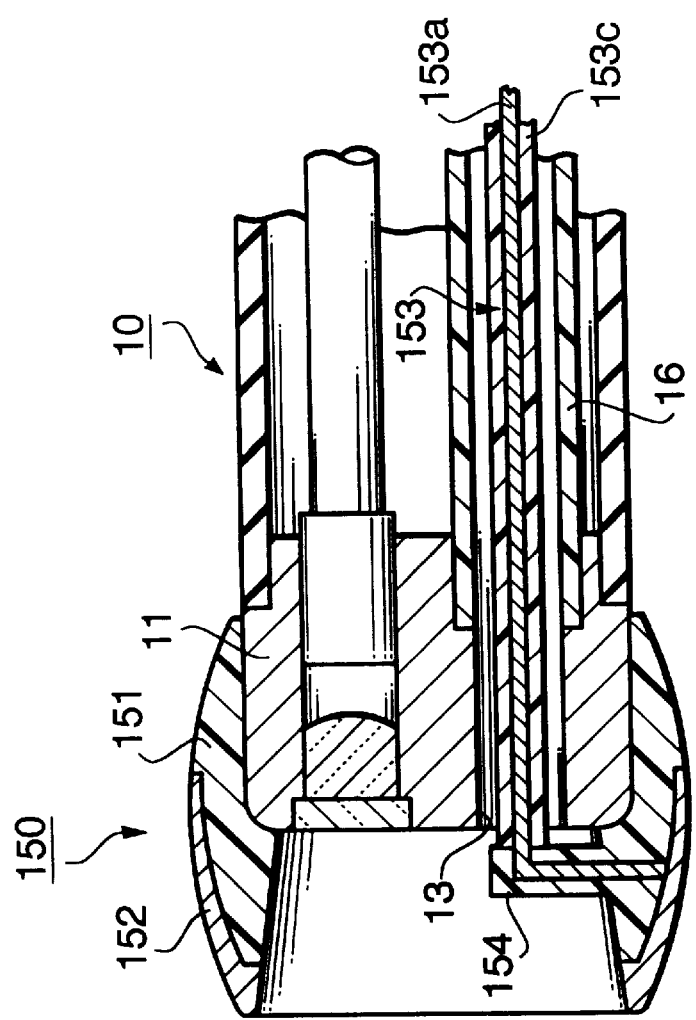
FIG. 16 is a sectional view of an electric cautery of the third embodiment.

The third embodiment of the present invention is described. FIGS. 16 and 17 are a sectional view and a front view of an electric cautery 150 of the third embodiment (mounted to the insertion part 10). In the third embodiment, the insertion part 10 is the same as that of the first embodiment.

The electric cautery 150 includes a spherical-shaped hood 151 mounted to the insertion part 10. The hood 151 is made of an insulating plastic which is transparent. The hood 151 is mounted to the distal end portion 11 of the insertion part 10 so that the distal end portion 11 is fit into the hood 151. The hood 151 can be detached from the distal end portion 11 of the insertion part 10. It is alternatively possible to provide threads on the hood 151 and the distal end portion 11 so that the hood 151 is mounted to the distal end portion 11 by thread engagement.

An electrode 152 is provided to the outer surface of the hood 151. The electrode 152 covers the tip of the hood 151 and the front half of the outer surface of the hood 151. In order to supply electricity to the electrode 152, a cable 153 is connected to the electrode 152. The cable 153 includes a lead wire 153a and a sheath 153c. The tip of the cable 153 is fixed to a protrusion 154 formed on the inner surface of the hood 151. The lead wire 153a further extends in the hood 151 (via the protrusion 154) and reaches the electrode 152, so that the lead wire 153a and the electrode 152 are connected.

The outer diameter of the cable 153 is smaller than the inner diameter of the suction channel 16. Further, there is a distance between the suction opening 13 and the protrusion 154 so that the protrusion 154 does not interfere with the suction. Thus, it is possible to perform suction through a suction opening 13.

Figure 18:
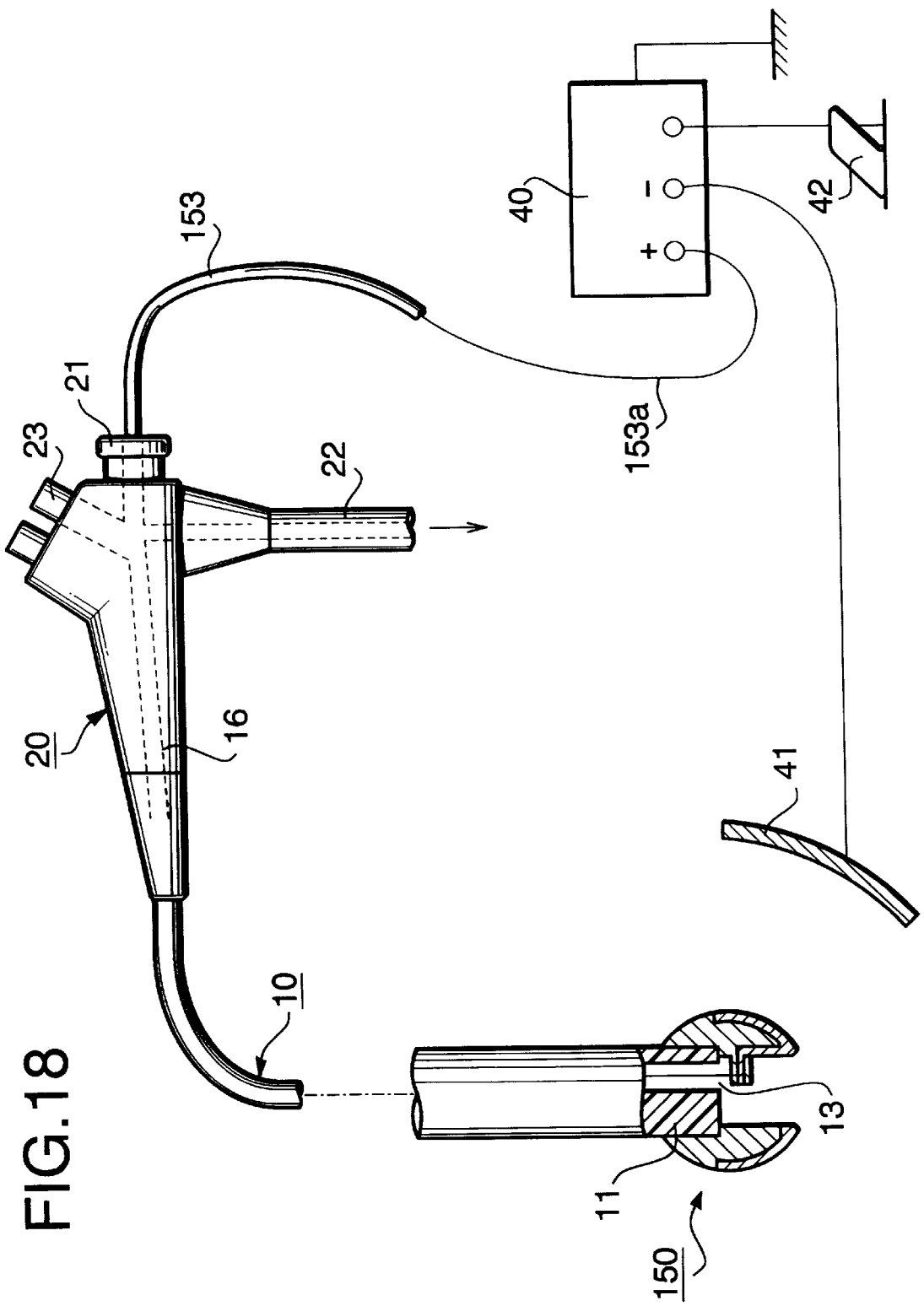
FIG. 18 is a schematic view of a system for operating the electric cautery of FIG. 16.

FIG. 18 is a schematic view illustrating a system for operating the electric cautery 150. The operation part 20 and the power source 40 are the same as those of the first embodiment. The lead wire 153a of the cable 153 is connected to a plus terminal of the power source 40. The system includes a contact plate 41 attached to the surface of the human body 1. The contact plate 41 is connected to the minus terminal of the power source 40 via a lead wire. That is, voltages of reversed polarity are applied to the electrode 152 and the contact plate 41.

Figure 19:
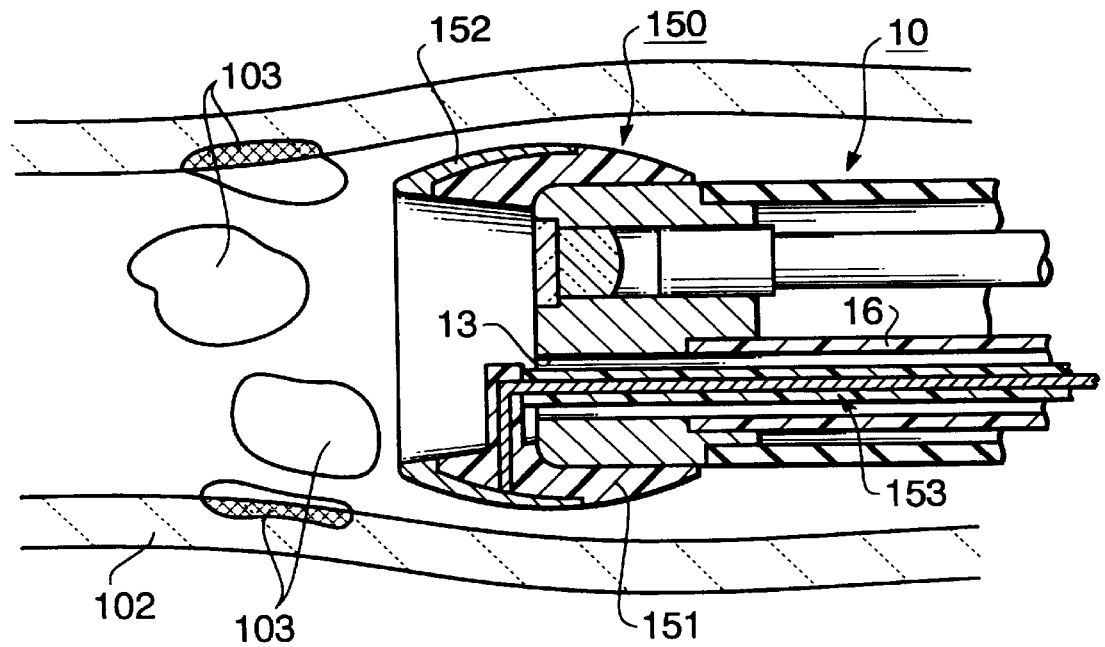
FIG. 19 is a sectional view of the operating electric cautery of FIG. 16.
Figure 20:
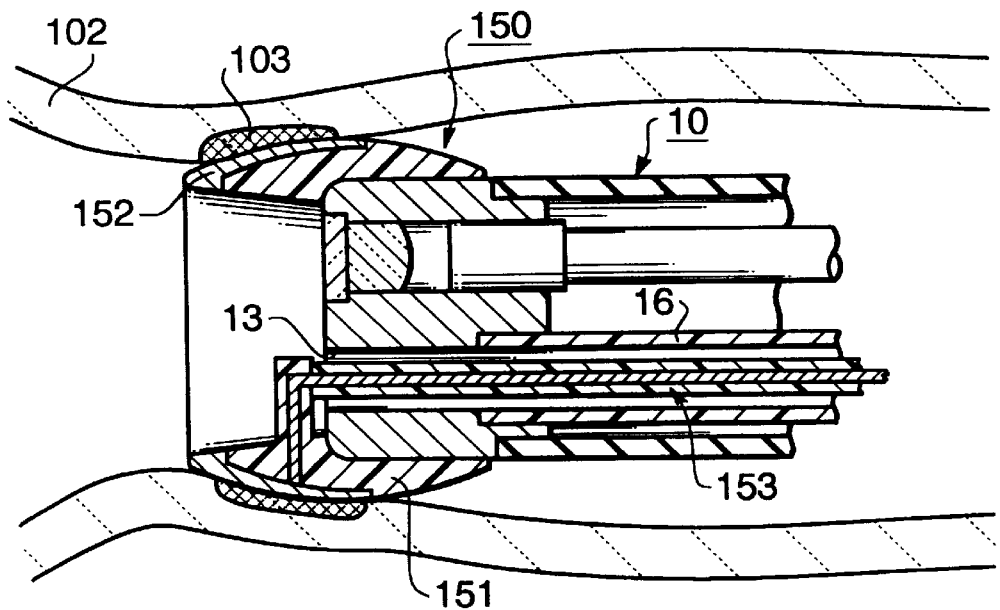
FIG. 20 is a sectional view of the operating electric cautery of FIG. 16.

FIGS. 19 and 20 are sectional views illustrating an example of operation of the electric cautery 150. In the example, ulcer 103 is formed on the inner surface of the laminal cavity 102. The electric cautery 150 (mounted to the insertion part 10) is inserted into the laminal cavity 102. In this example, the inner diameter of the laminal cavity 102 is larger than the outer diameter of the electric cautery 150 as shown in FIG. 19. In such case, when the suction is performed, the laminal cavity 102 is contracted so that the inner diameter of the laminal cavity 102 is reduced as shown in FIG. 20. Thus, the electrode 152 contacts throughout the inner surface of the laminal cavity 102, so that the electrode 152 efficiently cauterizes the ulcer 103.

As described above, according to the third embodiment, since the electrode 152 is provided to the outer surface of the hood 151, it is possible to efficiently cauterize large areas of the surface of the human body cavity. Further, since the laminal cavity 102 is contracted by suction, the electrode 52 sufficiently contacts the surface of the cavity. This may enable efficient cauterizing.

Figure 21:
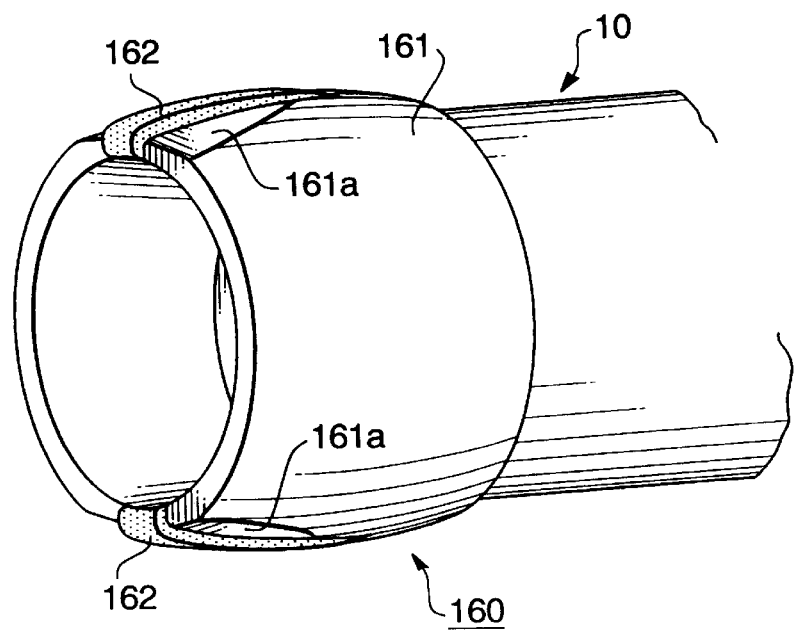
FIG. 21 is a perspective view of the electric cautery of a modification of the third embodiment.

FIG. 21 is a perspective view illustrating a modification of the third embodiment. In this modification, two electrodes 162 are provided to the opposing outer surface of a hood 161. The parts 161a of the outer surface of the hood 161 to which the electrodes 162 are provided are flattened so that the electrodes 162 are protruded from the flat surface 161a.

Figure 22:
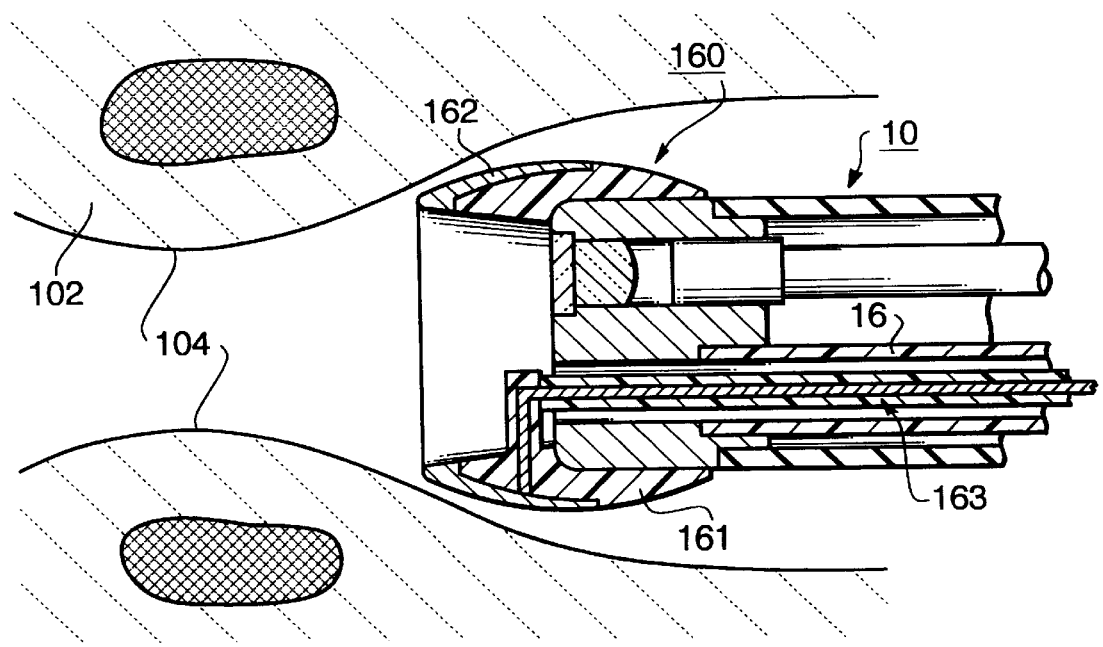
FIG. 22 is a sectional view of the operating electric cautery of FIG. 21.
Figure 23:
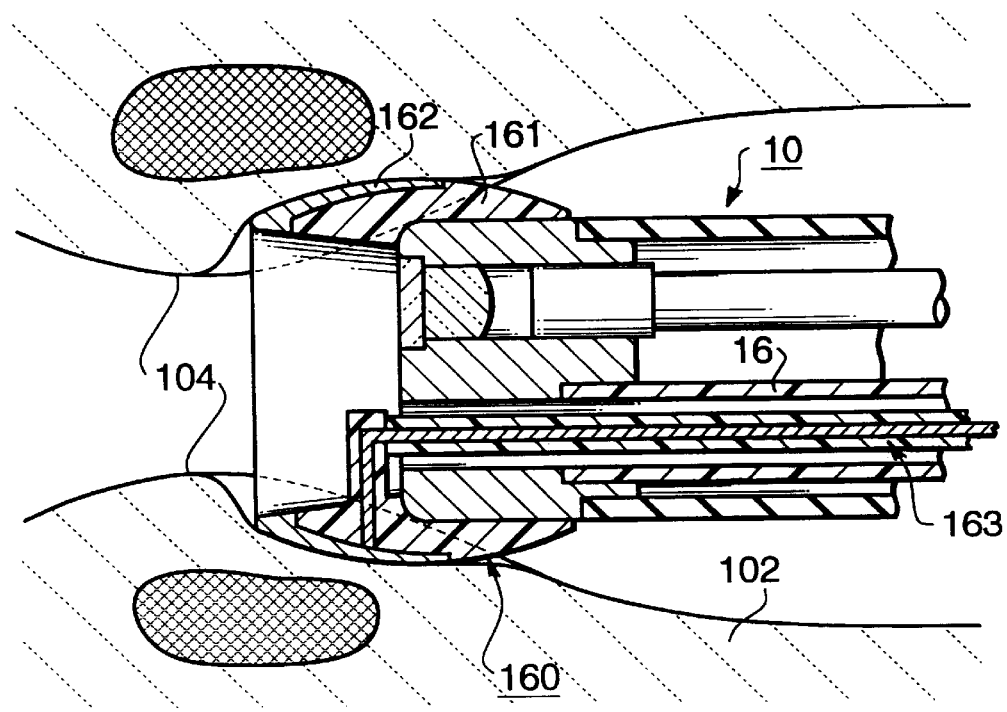
FIG. 23 is a sectional view of the operating electric cautery of FIG. 21.

FIGS. 22 and 23 are sectional views illustrating the example of the operation of the electric cautery 160. In this example, the electric cautery 160 is used to cut the isthmus 104 of the cavity 102. As shown in FIG. 22, the electric cautery 160 (and the insertion part 10) is moved toward the isthmus 104 in a state the electric cautery 162 is heated. With this, the electrodes 162 cut the isthmus 104 while cauterizing the cut portion of the isthmus 104 as shown in FIG. 23. Further, by operating a suction when cutting the isthmus 104, the inner surface of the isthmus 104 is moved closer to the hood 161.

[Fourth Embodiment]

Figure 24:
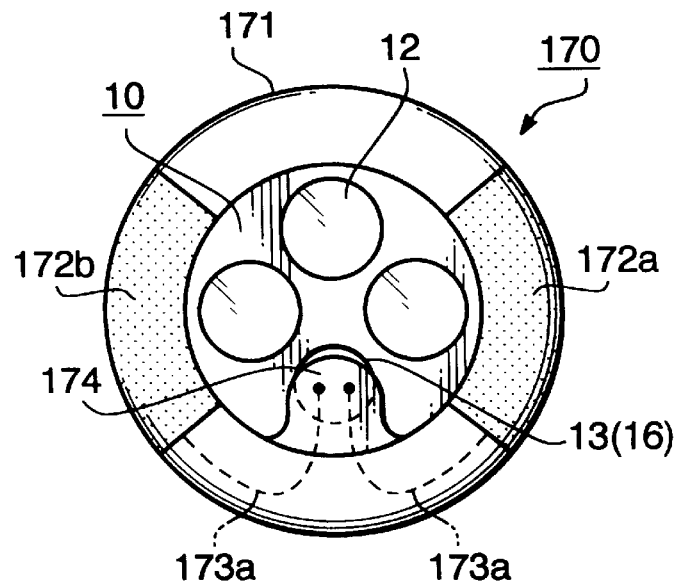
FIG. 24 is a front view of an electric cautery of a fourth embodiment.

The fourth embodiment of the present invention is described. FIG. 24 is a front view of the electric cautery 170. The electric cautery 170 has a hood 171 mounted to the insertion part 10. Similar to the third embodiment, the hood 171 is detachably mounted to the distal end portion 11 of the insertion part 10. Two electrodes 172a and 172b are formed on the opposing outer surfaces of the hood 171. A cable 173

(FIG. 26) is inserted through the channel 16 of the insertion part 10 and is fixed to a protrusion 174 formed on the inner surface of the hood 171. The lead wires 173a and 173b are extended in the protrusion 174 to reach the electrodes 172a and 172b, so that the lead wires 173a and 173b are connected to the electrodes 172a and 172b.

Figure 25:
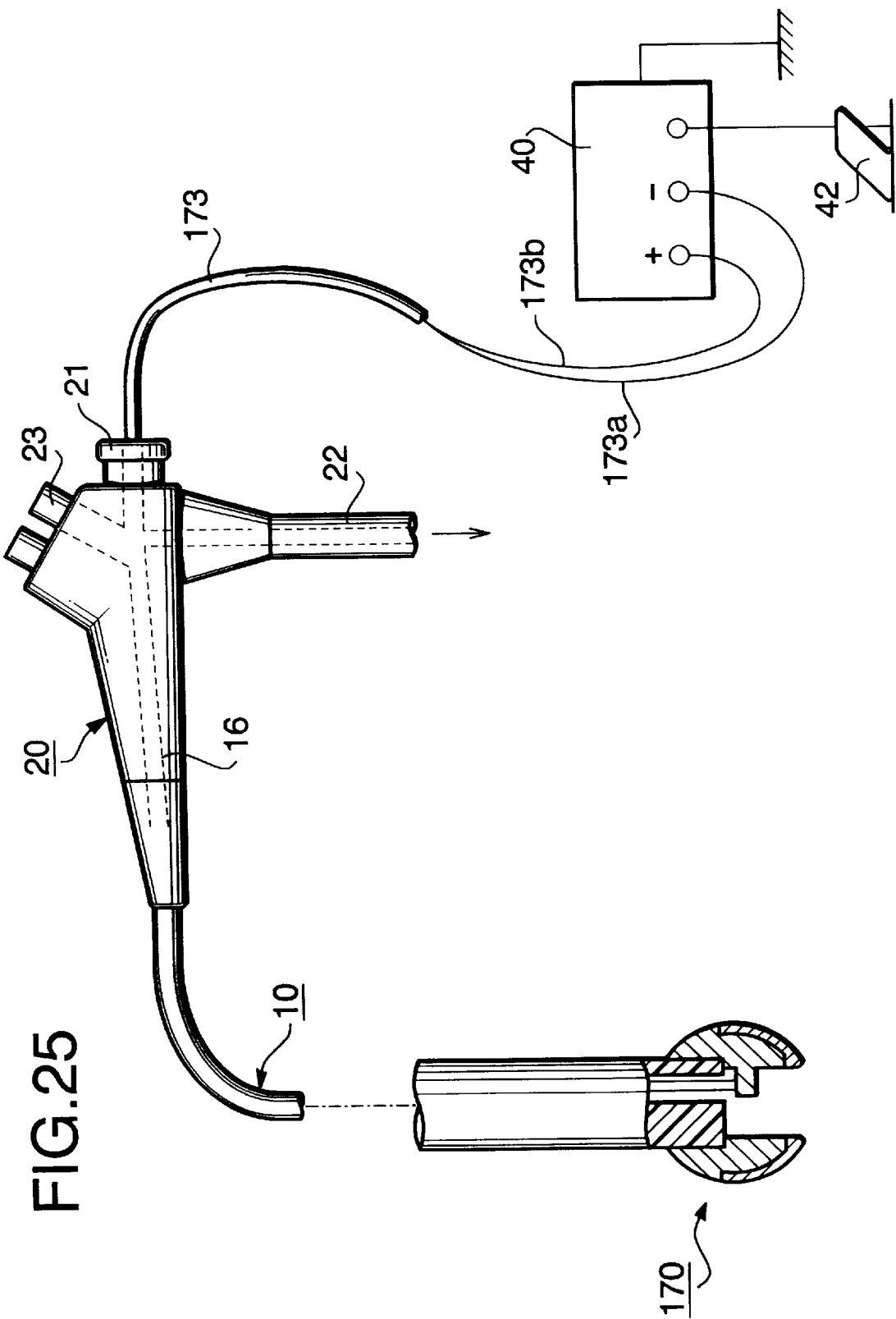
FIG. 25 is a schematic view of a system for operating the electric cautery of FIG. 24.
Figure 26:
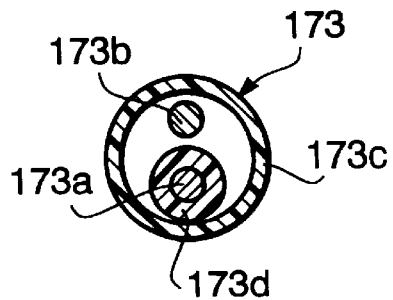
FIG. 26 is a schematic view of a cable in the electric cautery of FIG. 24.

FIG. 25 is a schematic view illustrating a system for operating the electric cautery 170. The operation part 20 and the power source 40 are the same as those of the second embodiment. The lead wire 173a is connected to a plus terminal of the power source 40, while the lead wire 173b is connected to a minus terminal of the power source 40. As shown in FIG. 26, the lead wires 173 and 173b are supported in a sheath 173c. In order to separate the lead wires 173a and 173b with each other, the lead wire 173a is covered by an insulation cover 173d. The operation of electric cautery 170 is the same as that of the third embodiment.

According to the fourth embodiment, similar to the third embodiment, it is possible to cauterize a large area of the surface of the human body cavity. Further, since plus and minus voltages are respectively applied to the electrodes 172a and 172b, it is not necessary to provide a contact plate 41 (of the third embodiment). That is, the structure of the electric cautery can be remarkably simple.

Figure 27A:
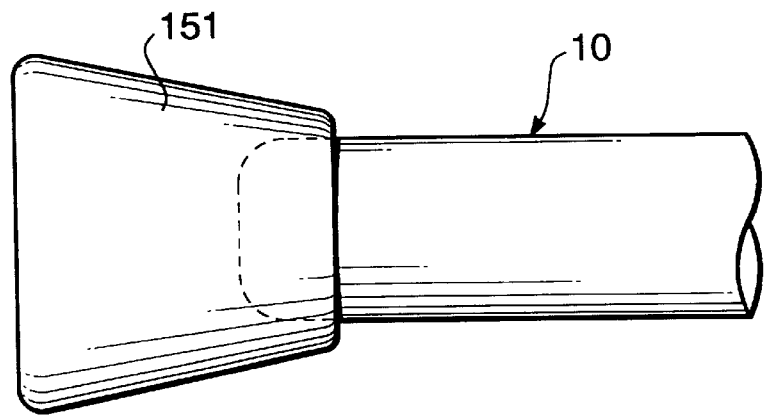
FIGS. 27A and 27B are side views showing examples of the shape of the hood of the third and forth embodiment.
Figure 27B:
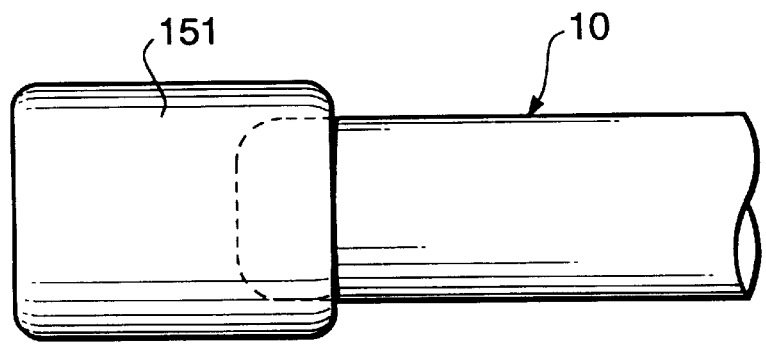

FIGS. 27A and 27B are side views showing other examples of the hood of the third and forth embodiments. The hood 151 may be bell-shaped (as shown in FIG. 27A), cylindrical-shaped (as shown in FIG. 27B), or the like.

Figure 28:
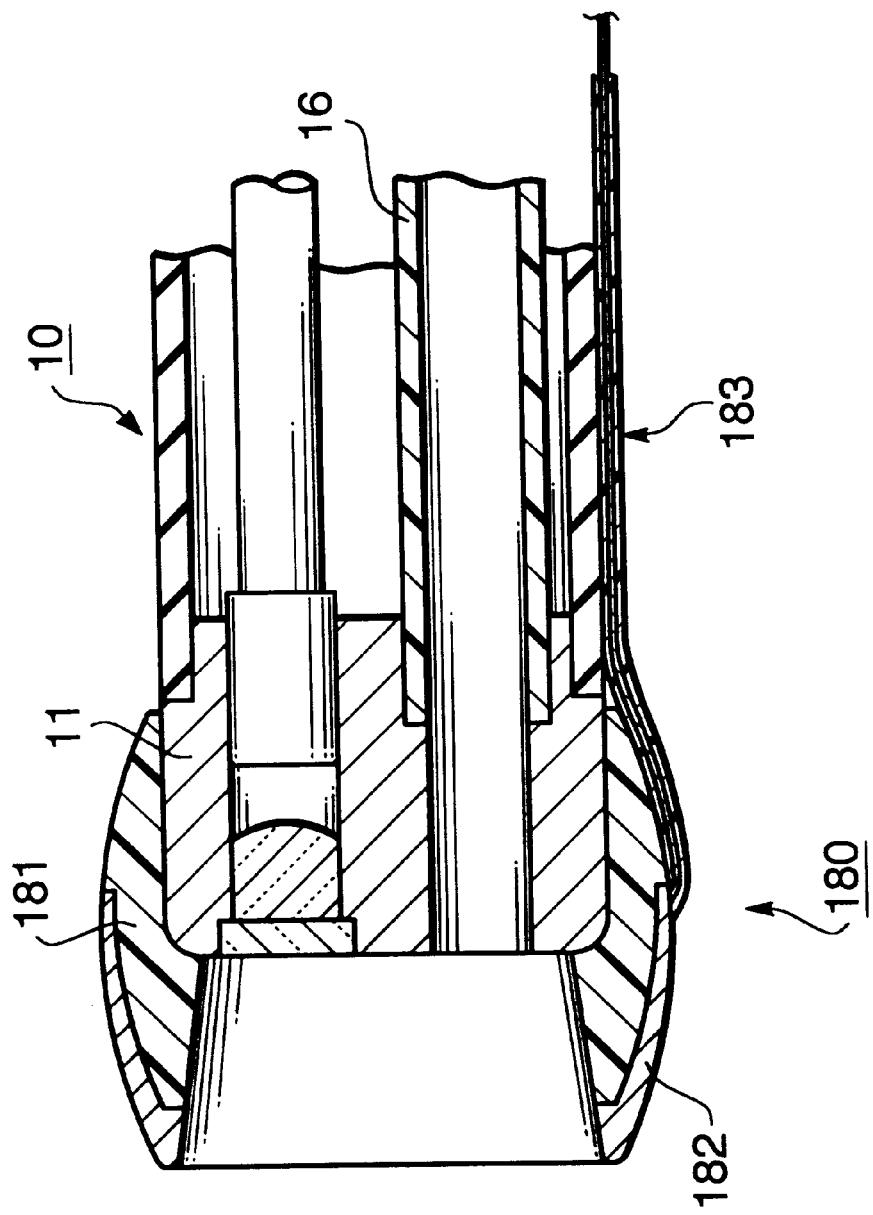
FIG. 28 is a sectional view of an electric cautery of a modification of the third and forth embodiment.

FIG. 28 is a sectional view showing a modification of the third and fourth embodiment. A hood 181 of this modification has an electrode 182 formed on an outer surface thereof and a tip thereof. Further, a cable 183 for supplying electricity to the electrode 182 is provided to the outer surface of the insertion part 10.

[Fifth Embodiment]

Figure 29:
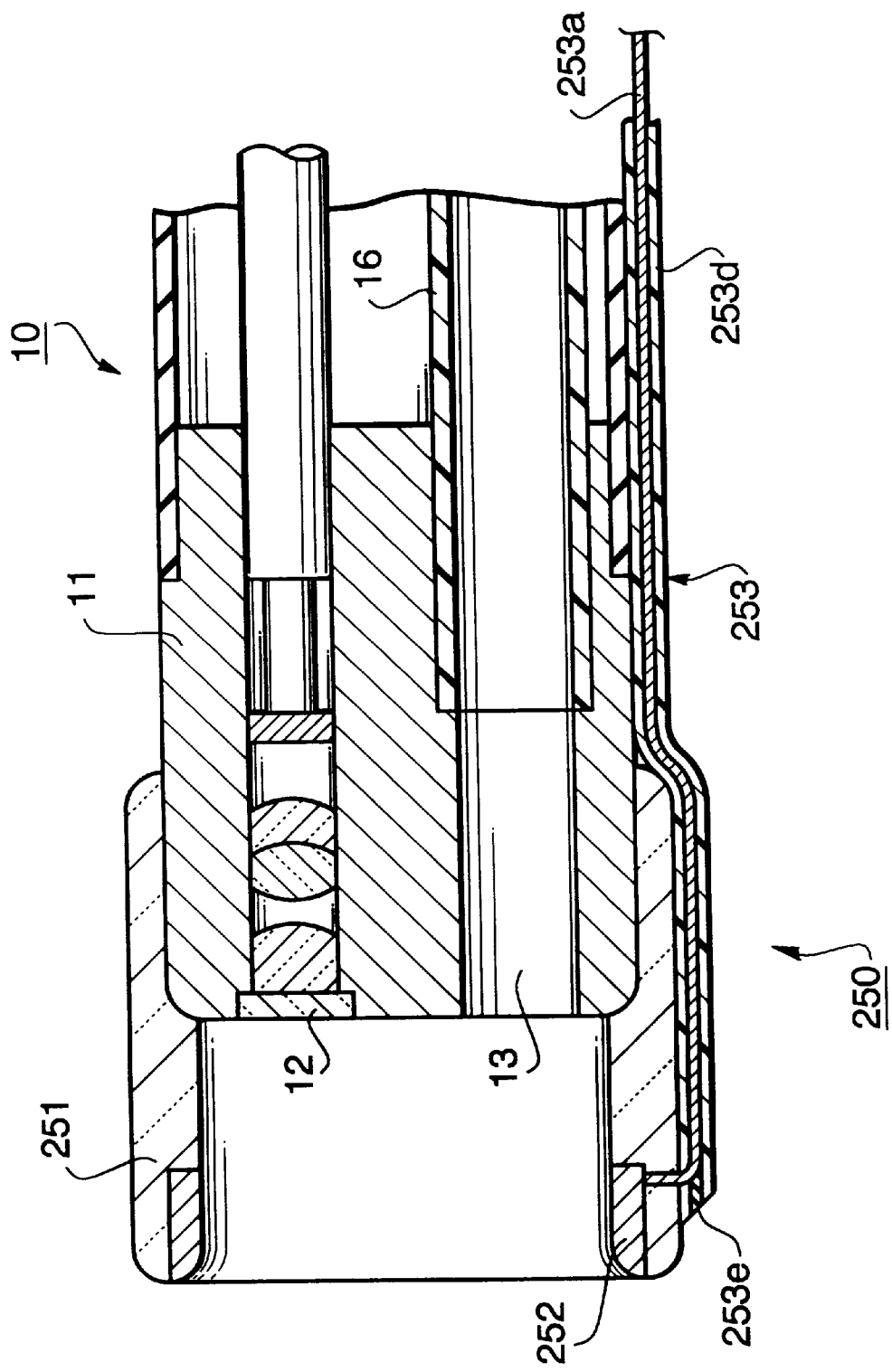
FIG. 29 is a sectional view of an electric cautery of a fifth embodiment of the present invention.

The fifth embodiment of the present invention is described. FIG. 29 is a sectional view of an electric cautery 250 of the fifth embodiment mounted to the insertion part 10. In the fifth embodiment, the structure of the insertion part 10 is the same as that of the first embodiment.

As shown in FIG. 29, the electric cautery 250 has a hood 251 mounted to the insertion part 10. The hood 251 is detachably mounted to the distal end portion 11 of the insertion part 10 so that the distal end portion 11 is fit into the hood 251. The hood 251 is made of an insulating plastic which is transparent. It is alternatively possible to provide threads on the hood 251 and the distal end portion 11 so that the hood 251 is mounted to the distal end portion 11 by thread engagement.

An electrode 252 is formed on the inner surface of the hood 251. In order to supply electricity to the electrode 252, a cable 253 is provided to the outer surface of the insertion part 10. The cable 253 includes a lead wire 253a and a sheath 253d covering the lead wire 253a. The sheath 253d is attached to the outer surface of the insertion part 10 and the hood 251. The lead wire 253a extends out of a tip of the cable 253. The lead wire 253a further penetrates the hood 251 and reaches the electrode 252, so that the lead wire 253a is connected to the electrode 252. In order to prevent a water intrusion, a distal end of the cable 253 is filled with a silicon seal member 253e.

Figure 30:
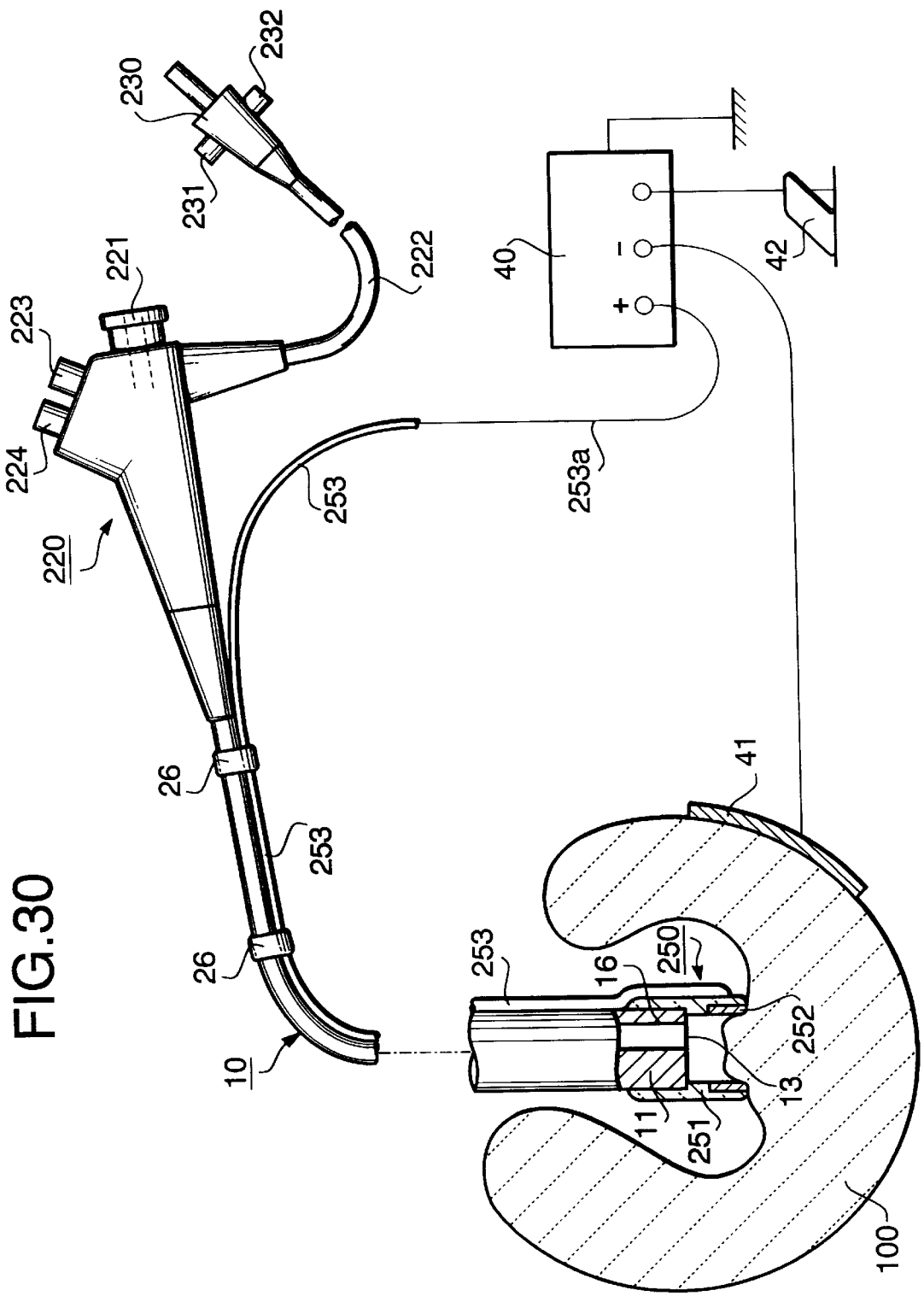
FIG. 30 is a schematic view of a system for operating the electric cautery of FIG. 29.

FIG. 30 is a schematic view illustrating a system for operating the electric cautery 250. The proximal end of the insertion part 10 is fixed to an operation part 220. The suction channel 16 is extended through the operation part 220 and leads to an opening 221 for inserting an instrument such as a forceps, a snare, or the like. A connection tube 222 is branched from the suction channel 16 and reaches a connector 230. A connector 230 has an air/water port 231 to be connected to an air/water source and a suction port 232 to be connected to a suction apparatus. The operation part 220 has a suction bulb 223 for controlling the suction via the suction channel 16 and a air/water bulb 224 for controlling the supply of air/water.

The cable 253 is fixed to the outer surface of the insertion part 10 by several tapes 26 made of silicon rubber or the like. The lead wire 253a of the cable 253 is connected to the plus terminal of the power source 40. A contact plate 41 is attached to the surface of the human body 100 and is connected to the minus terminal of the power source 40 via a lead wire. That is, voltages of reversed polarity are applied to the electrode 252 and the contact plate 41.

Figure 31:
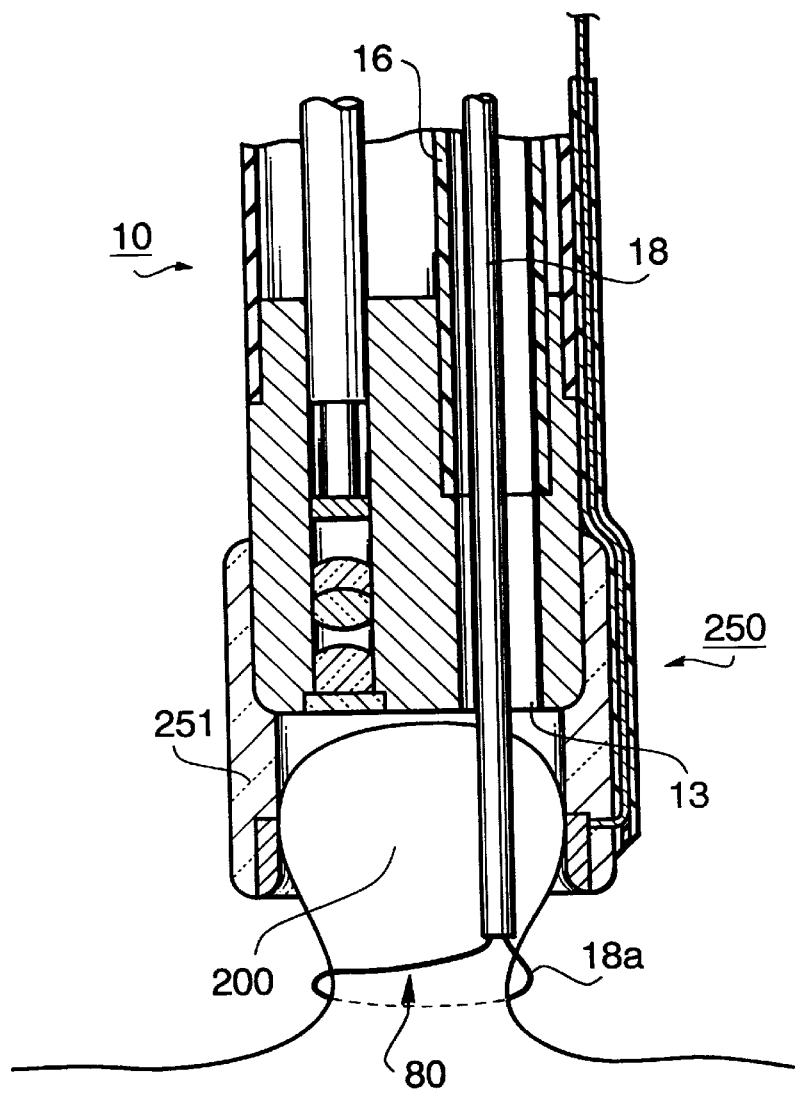
FIG. 31 is a schematic view of the operating electric cautery of FIG. 29.
Figure 32:
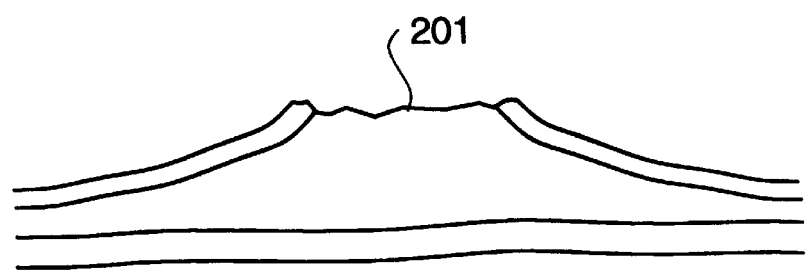
FIG. 32 is a schematic view of a surface of a human body cavity.
Figure 33:
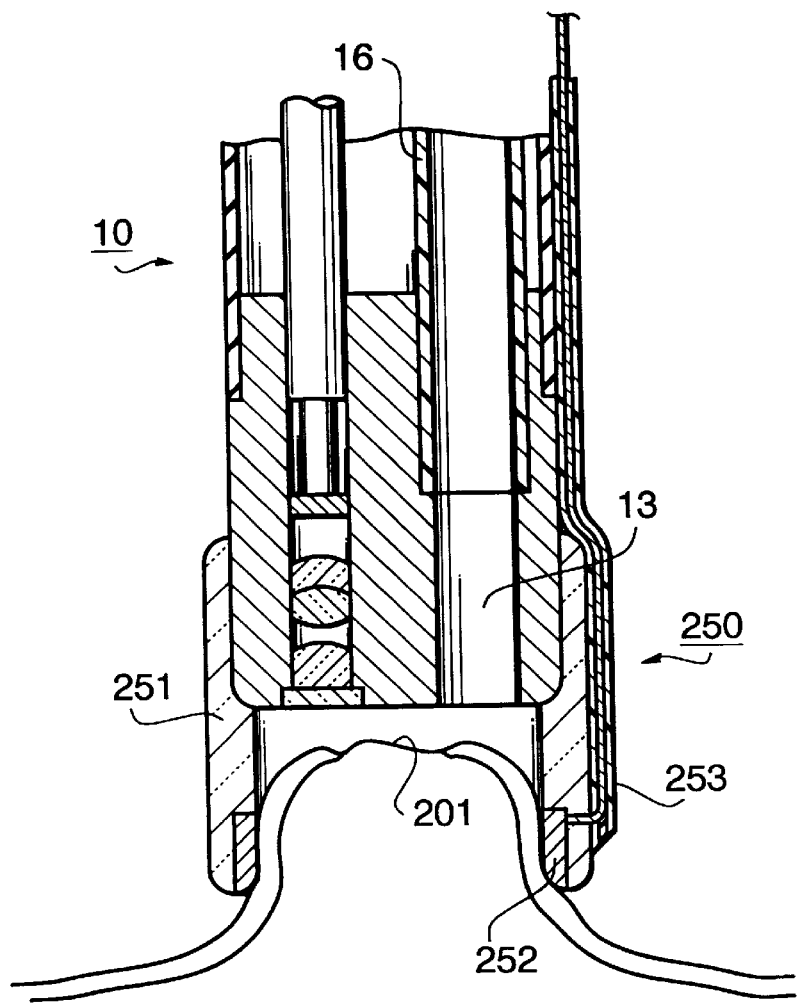
FIG. 33 is a schematic view of the operating electric cautery of FIG. 29.
Figure 34:
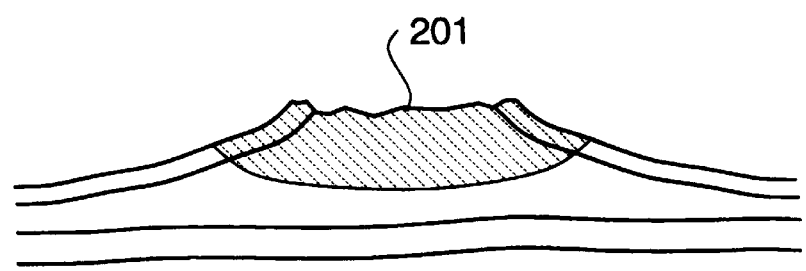
FIG. 34 is a schematic view of a surface of a human body cavity.

FIGS. 31 through 34 illustrate the operation of the electric cautery 250. First, an operator inserts a high-frequency snare 18 through the suction channel 16. Then, the operator turns the suction bulb 223 to start suction (via the suction channel 16). With this, the surface of the human body cavity suffering ulcer (or cancer or the like) is sucked in the hood 251 as shown in FIG. 31. It causes a polyp 200 in the hood 251. Then, the operator cuts the polyp 200 using the high-frequency snare 18. FIG. 32 shows the surface 201 of the human body cavity, after the polyp 200 is removed. In order to cauterize the surface 201 of the human body cavity, the operator turns the suction bulb 223 to start suction again. With this, the surface 201 of the human body cavity is again sucked in the hood 251 as shown in FIG. 33. Further, the operator turns on the switch 42 to apply high-frequency voltage to the electrode 252, thereby to cauterize the surface 201 as shown by crosshatching in FIG. 34. Thus, the blood from the ends of blood lines 102 is clot.

According to the fifth embodiment, since the electrode 252 is formed on the inner surface of the hood 251, it is possible to cauterize a large area of the surface of the human body cavity. Further, since the cable 253 is located at the outer surface of the insertion part 10, the suction channel 16 can be used for inserting another instrument such as a snare, a forceps or the like. Thus, it is possible to use the electric cautery 250 and other instrument at the same time.

Figure 35:
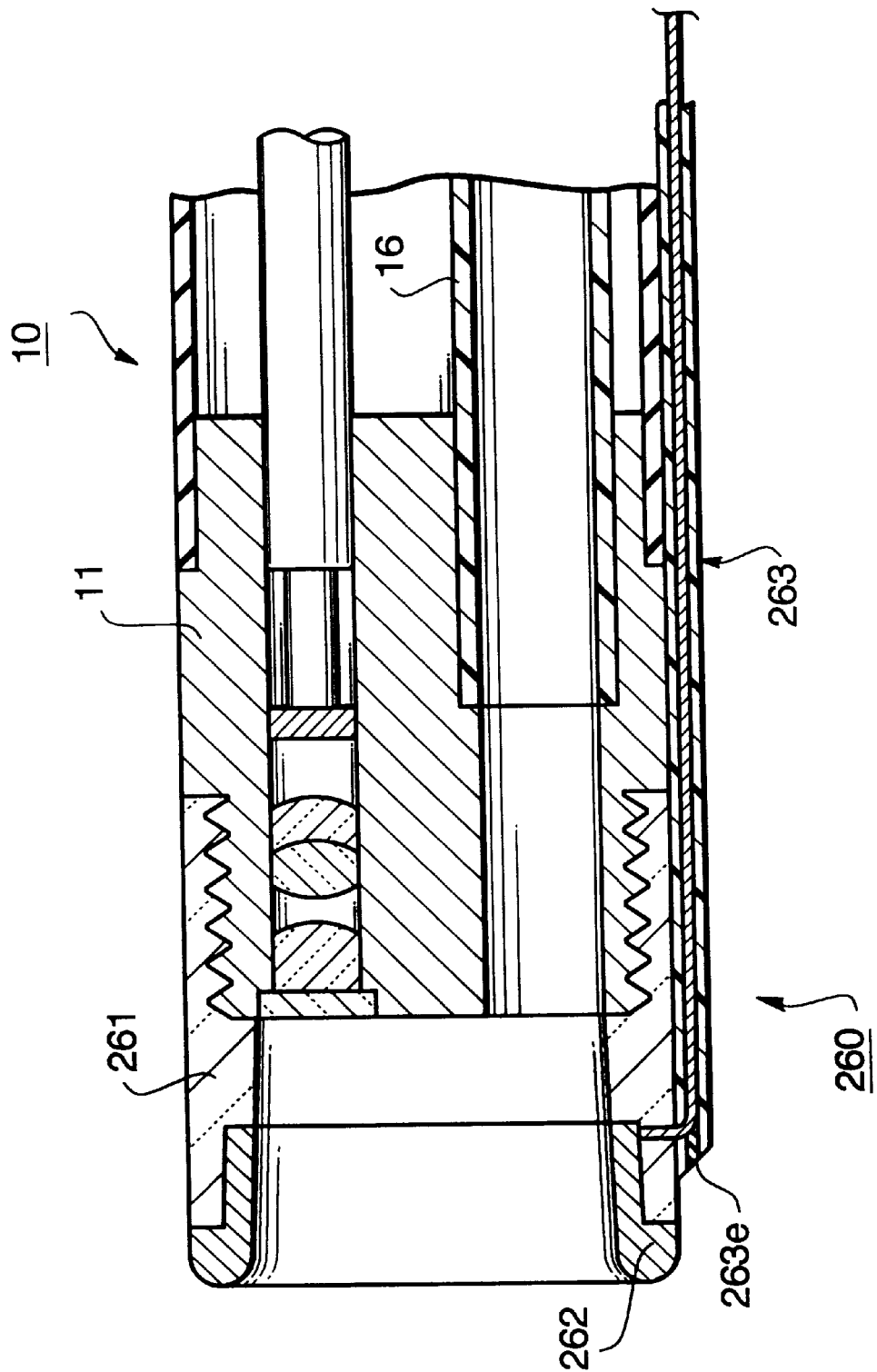
FIG. 35 is a sectional view of an electric cautery of a modification of the fifth embodiment.

FIG. 35 is a sectional view illustrating the modification of the fifth embodiment. A hood 261 of this modification is detachably mounted to the distal end portion 11 of the insertion part 10 by threading engagement. An electrode 262 of this modification is provided to the tip of the hood 261. The electrode 262 circumferentially extends along the tip of the hood 261 as well as the inner surface of the hood 261. With such an arrangement, when the hood 261 abuts the surface of the human body cavity, the electrode 262 deeply contacts the surface. This may enable efficient cauterizing.

[Sixth Embodiment]

Figures 36, 37:
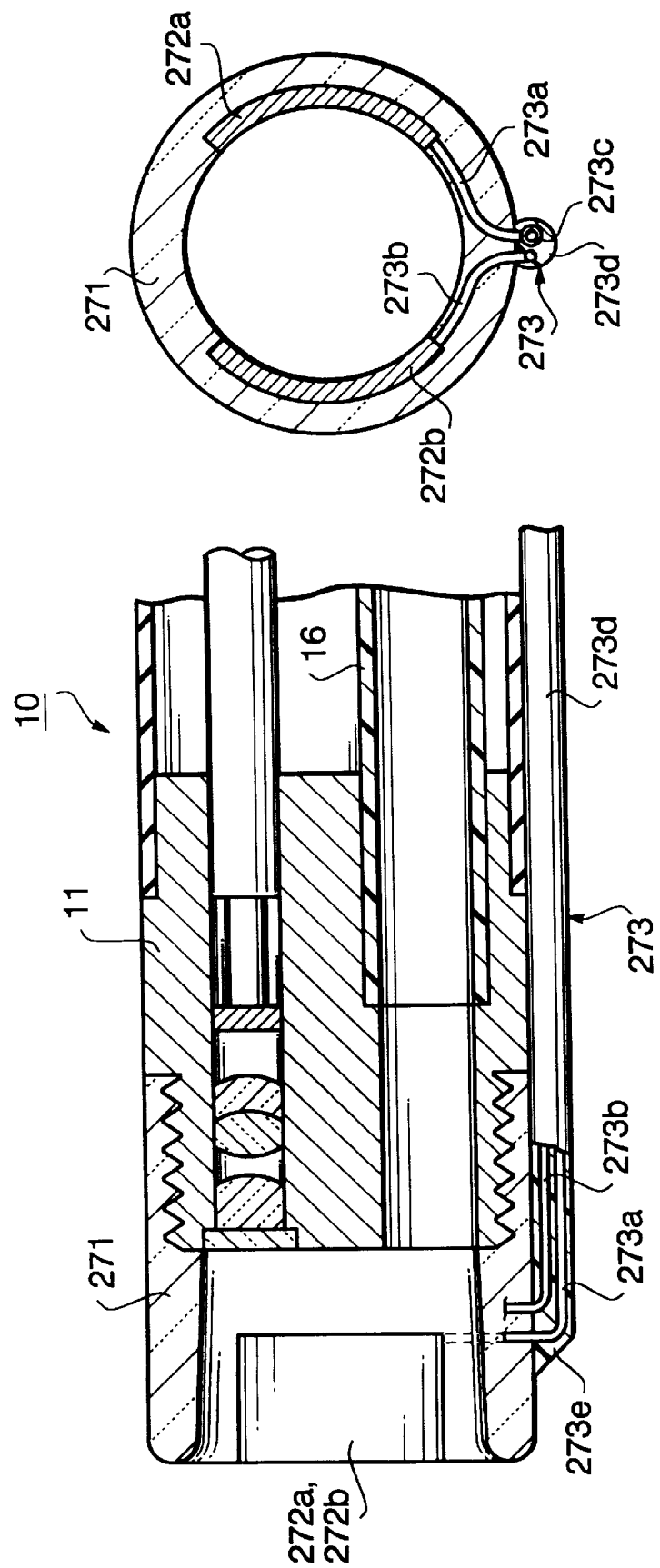
FIG. 36 is a sectional view of an electric cautery of a sixth embodiment.
FIG. 37 is a front view of the electric cautery of FIG. 36.

The sixth embodiment of the present invention is described. FIG. 36 is a sectional view of the electric cautery 270 mounted to the insertion part 10. FIG. 37 is a front view of the electric cautery 270. The insertion part 10 of the sixth embodiment is provided with a external thread formed at the distal end portion 11. Other structure of the insertion part 10 is the same as that of the first embodiment.

As shown in FIGS. 36 and 37, the electric cautery 270 has a hood 271 mounted to the insertion part 10. The hood 271 has an internal thread which engages the external thread of the distal end portion 11 of the insertion part 10. With this, the hood 271 is detachably mounted to the insertion part 10.

Two electrodes 272a and 272b are formed on the opposing sides of the inner surface of the hood 271. In order to supply electricity to the electrodes 272a and 272b, a cable 273 is provided to the outer surface of the insertion part 10. The cable 273 includes two lead wires 273a and 273b and a sheath 273d covering the lead wires 273a and 273b. Further, in order to separate the lead wires 273a and 273b from each other, the lead wire 273 is covered by an insulation cover 273c. The sheath 273d is attached to the outer surface of the hood 271. The lead wires 273a and 273b extend out of the tip of the cable 273. The lead wires 273a and 273b further penetrate the hood 271 and respectively reach the electrode 272a and 272b, so that the lead wires 273a and 273b are connected to the electrode 272a and 272b. In order to prevent a water intrusion, the tip of the cable 273 is filled with a silicon seal member 273e.

FIG. 38 is a schematic view illustrating a system for operating the electric cautery 270. The structure of the operation part 220, the connector 230 and the power source 40 are the same as those of the fifth embodiment. The cable 273 is fixed to the insertion part 10 by several tapes 26 made of silicon rubber or the like. The lead wire 273a is connected to the plus terminal of the power source 40, while the lead wire 273b is connected to the minus terminal of the power source 40. That is, voltages of reversed polarity are applied to the electrodes 272a and 272b. With such an arrangement, the surface of the human body cavity can be cauterized without providing a contact plate 41 (FIG. 30) of the fifth embodiment.

Figure 39:
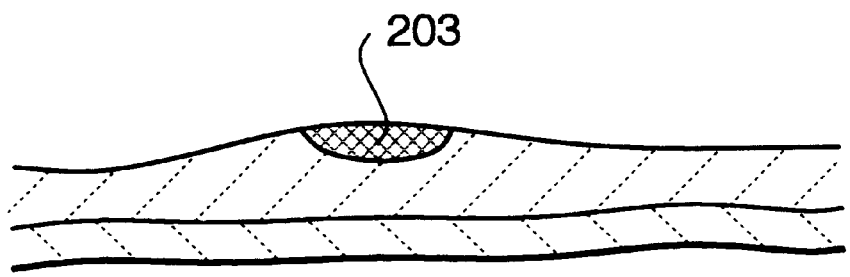
FIG. 39 is a schematic view showing a surface of a human body cavity.
Figure 40:
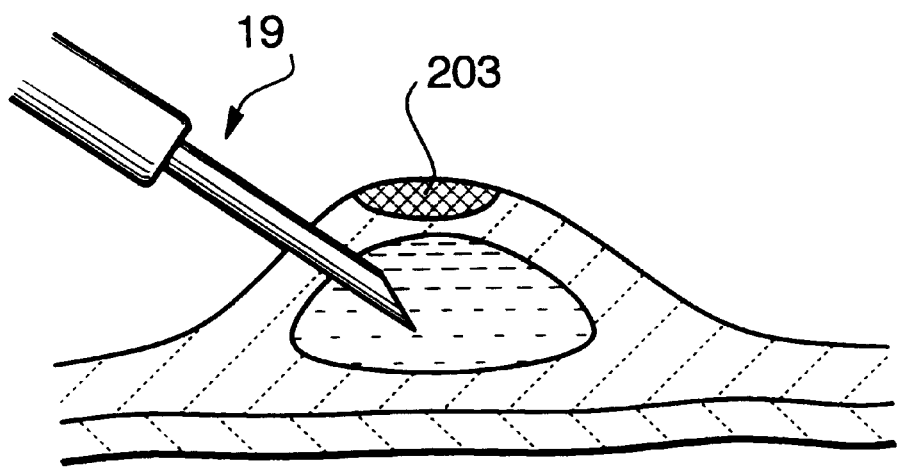
FIG. 40 is a schematic view showing a bulged surface of a human body cavity.
Figure 41:
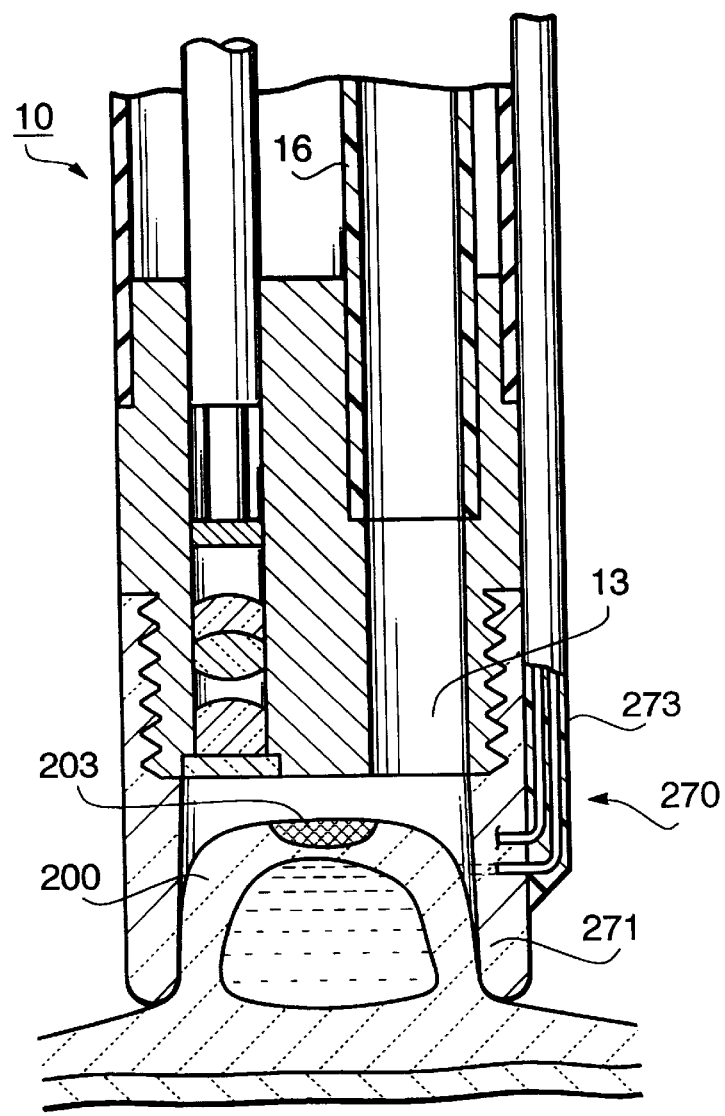
FIG. 41 is a sectional view of the operating electric cautery of FIG. 40.
Figure 42:
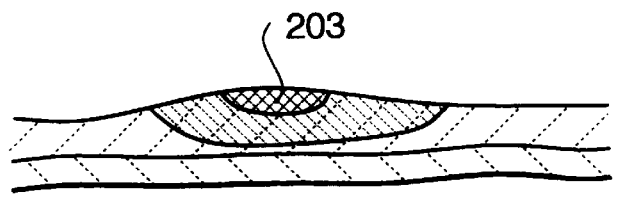
FIG. 42 is a schematic view showing a cauterized surface of a human body cavity.

FIGS. 39 through 42 illustrate an example of operation of the electric cautery 270. In this example, there is a blooding portion 203 on the surface of the human body cavity as shown in FIG. 39. First, an operator inserts an injector 19 through the suction channel 16 to the blooding portion 203. The operator injects liquid (by the injector 19) under the surface of the human body cavity so that the surface is bulged as shown in FIG. 40. Then, an operator turns the suction bulb 223 (FIG. 38) to start suction from the suction channel 16. With this, the bulged surface of the human body cavity is sucked in the hood 271 as shown in FIG. 41. Then, the operator turns on the switch 42 of the power source 40 (FIG. 38) to apply voltage to the electrode 272a and 272b, so that the surface of the human body cavity is cauterized as shown by crosshatching in FIG. 42. Thus, the blood is clot.

According to the sixth embodiment, since the electrode 252 is formed on the inner surface of the hood 251, it is possible to cauterize a large area of the surface of the human body cavity. Further, since the cable 253 is located at the outer surface of the insertion part 10, the suction channel 16 can be used for inserting another instrument such as an injector, a snare, a forceps or the like. Thus, it is possible to use the electric cautery 250 and other instrument at the same time.

[Seventh Embodiment]

Figure 43:
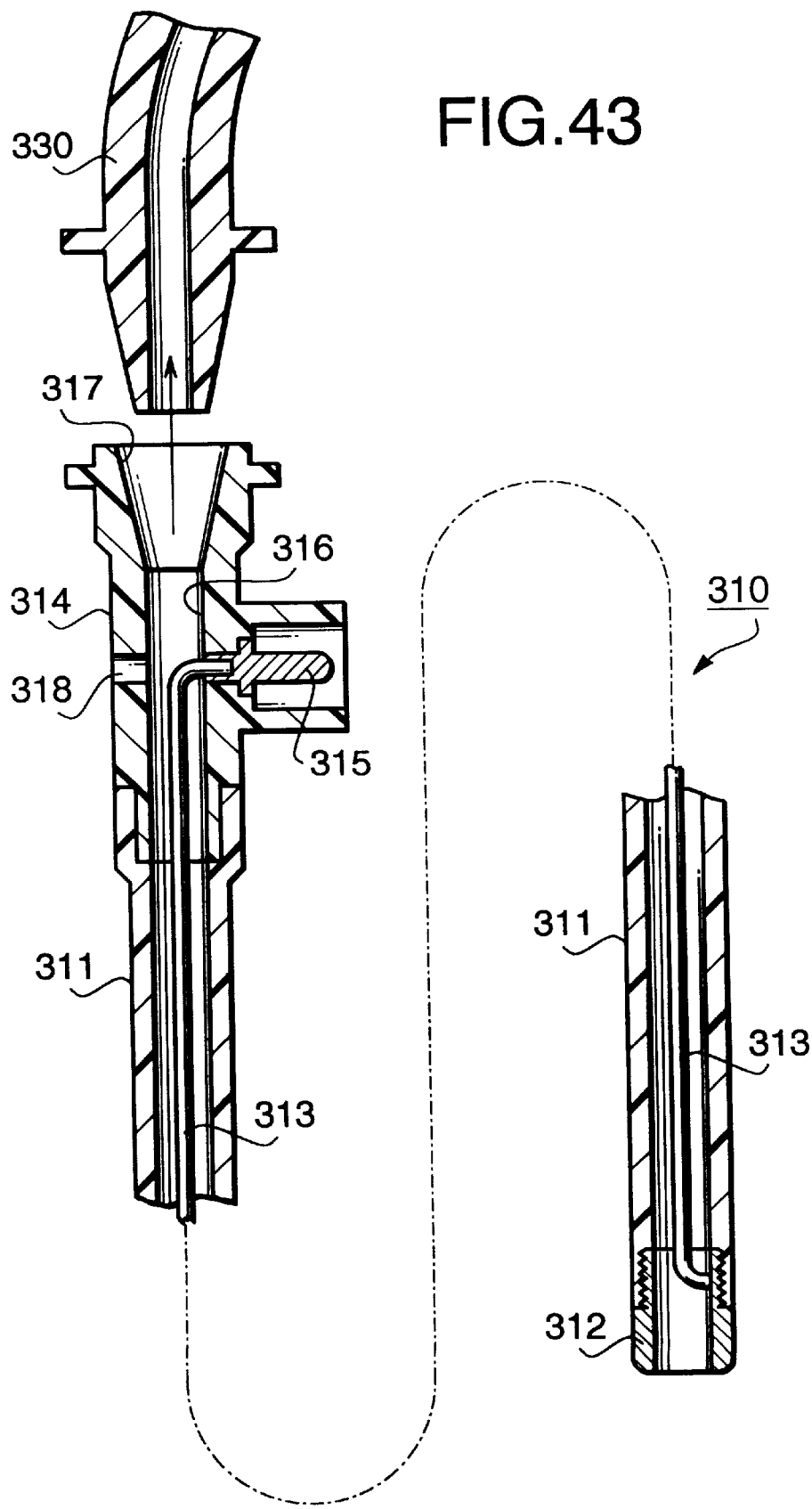
FIG. 43 is a sectional view of an electric cautery of a seventh embodiment.
Figure 44:
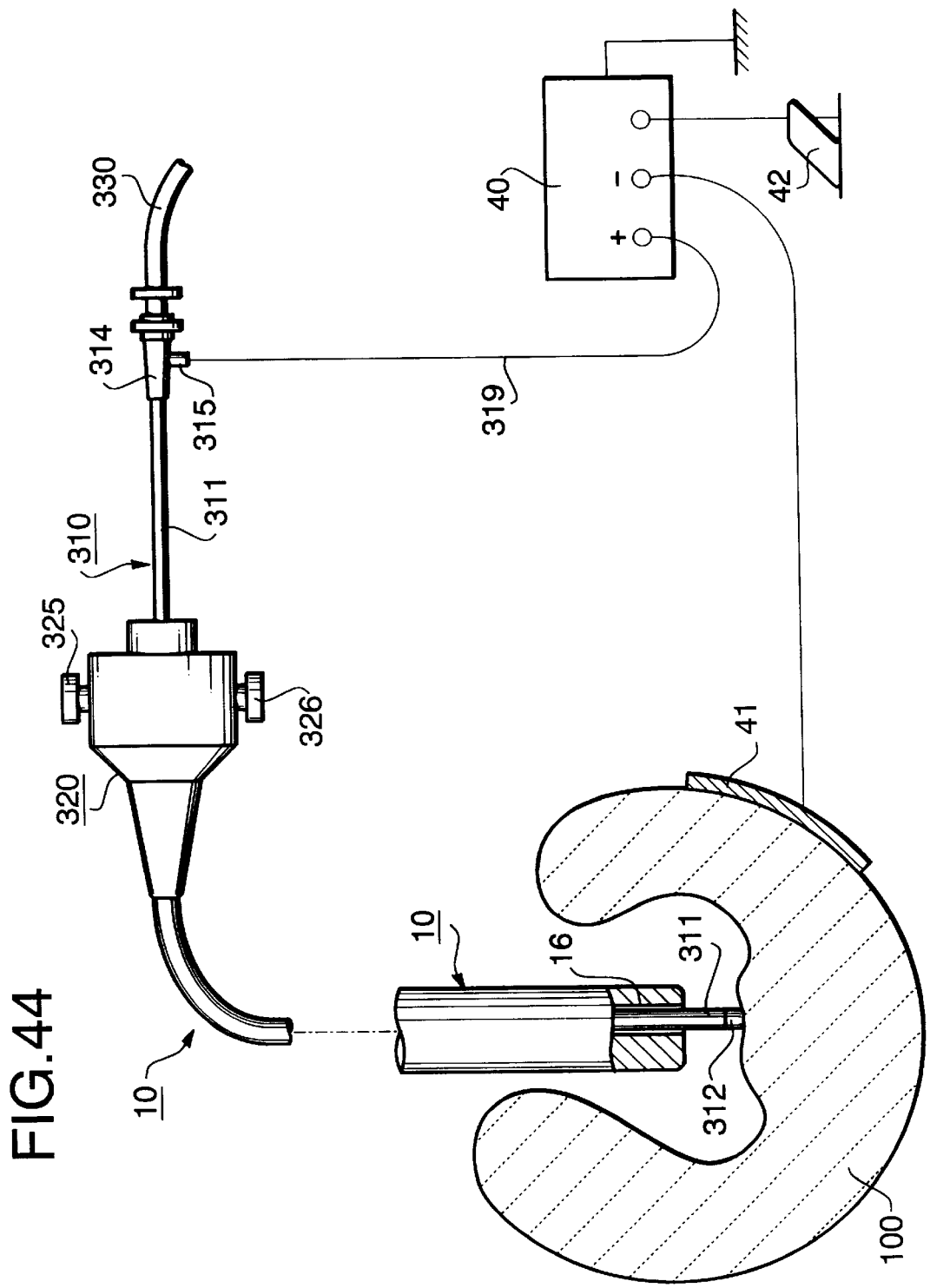
FIG. 44 is a schematic view of the electric cautery of FIG. 41.

The seventh embodiment of the present invention is described. FIG. 43 is a sectional view showing an electric cautery 310 of the seventh embodiment. FIG. 44 is a schematic view illustrating a system for operating the electric cautery 310.

As shown in FIG. 43, the electric cautery 310 includes a suction tube 311. The suction tube 311 is inserted through a channel 16 of the insertion part 10 (FIG. 44). An electrode 312 is fixed to the tip of the tube 311. The suction tube 311 is made of soft and insulating synthetic resin such as fluoro ethylene, polytetra-fluoroethylene and poly-propylene. The electrode 312 is mounted to the tip of the suction tube 311 by threading (or adhering).

The outer diameter of the electrode 312 is substantially the same as the suction tube 311. A proximal end of the suction tube 311 is connected to a connector 314. The connector 314 has a terminal 315 that is to be electrically connected to a power source 340 (FIG. 44). A lead wire 313 is provided in the suction tube 311. An end of the lead wire 313 is fixed to the electrode 312, while the other end of the lead wire 313 is fixed to the terminal 315 of the connector 314.

The connector 314 has a channel 316 which is connected to the suction tube 311 and a connecting portion 317 to be connected with a suction apparatus 330. The connecting portion 317 has a tapered surface which receives a joint of the suction apparatus 330. Further, the connector 314 has a leak hole 318 connected to the channel 316. When the suction apparatus 330 is turned on, external air enters from the leak hole 318 and flows in the channel 316. When the operator shields the leak hole 18 with his finger or the like, suction is performed through the suction tube 311.

As shown in FIG. 44, the proximal end of the insertion part 10 is connected to an operation part 320. The operation part 320 includes an air/water bulb 325 and a suction bulb 326. The electric cautery 310 is inserted from an opening provided at the rear end of the operation part 320 so that the electrode 312 contacts the human body cavity 100. The terminal 315 is electrically connected to the plus terminal of the power source 40 via a lead wire 319. With this, a plus voltage is applied to the lead wire 313 (that is, to the electrode 312). A contact plate 341 is attached to the surface of the human body 100 and is connected to the minus terminal of the power source 40 via another lead wire.

Figure 45:
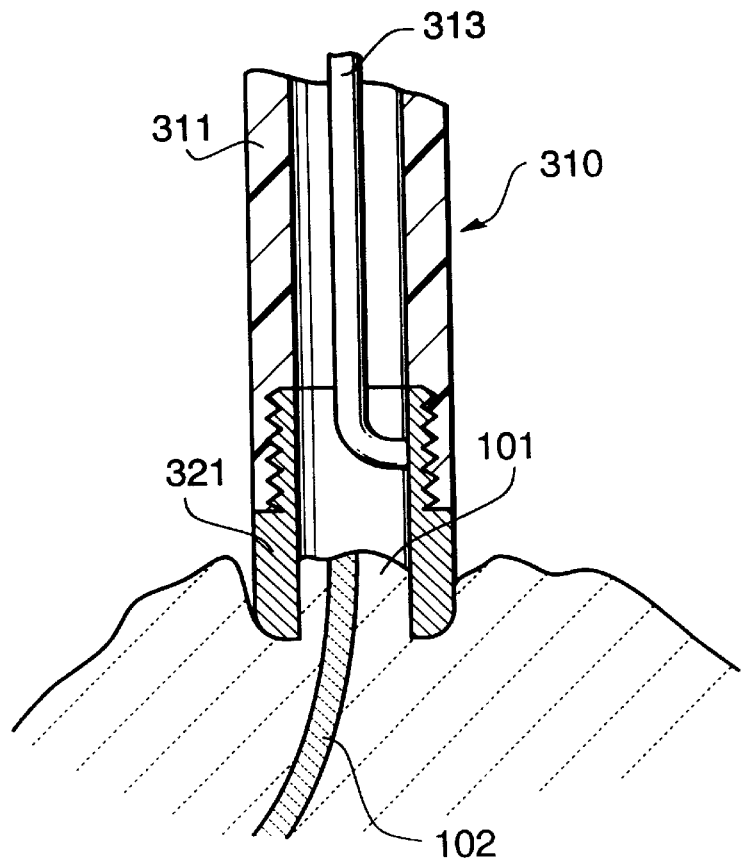
FIG. 45 is a sectional view of the operating electric cautery of FIG. 41.
Figure 46:
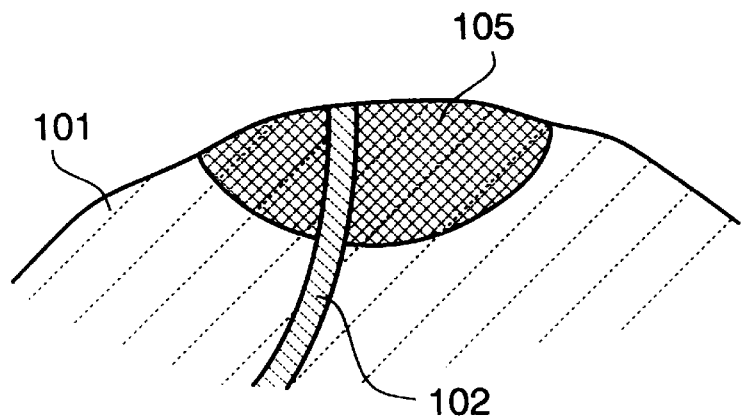
FIG. 46 is a schematic view of a cauterized surface of human body cavity.

The operation of the electric cautery 310 is described with reference to FIGS. 45 and 46. First, the operator urges the electrode 352 to the surface 101 of the human body cavity so that the tip of the electrode 352 surrounds an opening of a blood line 102. Then, the operator turns the suction bulb 326 (FIG. 44) to start suction by the suction tube 311. With this, the surface 101 of the human body is sucked in the electrode 312 as shown in FIG. 45. Then, the operator turns on the switch 42 of the power source 40 (FIG. 44) to apply voltage to the electrode 312, so that the surface 101 is cauterized. Ends of blood lines 102 may be opened on the surface 101 of the human body cavity. However, the surface 101 of the human body cavity is cauterized by electric cautery 310 as shown by crosshatching in. FIG. 46. Thus, the blood from the ends of blood lines 102 is clot.

According to the seventh embodiment, cauterization is performed by abutting the electrode 312 to the surface of the human body cavity and by suction. Thus, the complicated operation (like the operation of a biopsy forceps) is not necessary.

Figure 47:
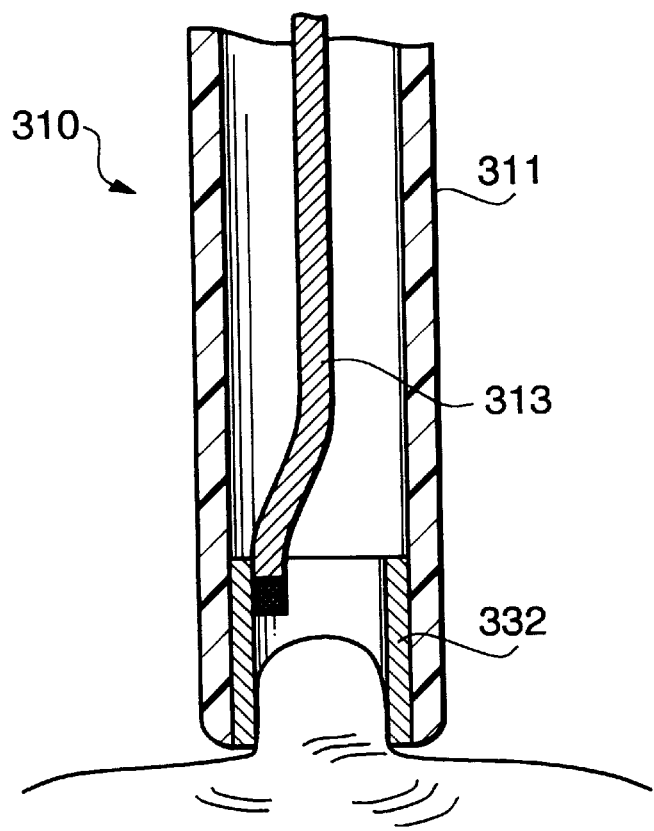
FIG. 47 is a sectional view of a cautery of a first modification of the seventh embodiment.
Figure 48:
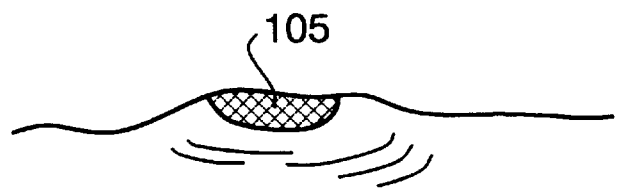
FIG. 48 is a schematic view of a cauterized surface of human body cavity.

FIG. 47 is a sectional view showing the first modification of the seventh embodiment. An electrode 332 of this first modification is cylindrical-shaped and is formed on the inner surface of the tip of the suction tube 311. The tip of the electrode 352 is aligned with the tip of the suction tube 311. The cable 313 is provided in the suction tube 311 and is attached to the inner surface of the electrode 352 by means of spot welding or the like. In this modification, it is possible to intensively cauterize a small area of the human body cavity as shown in FIG. 48.

Figure 49:
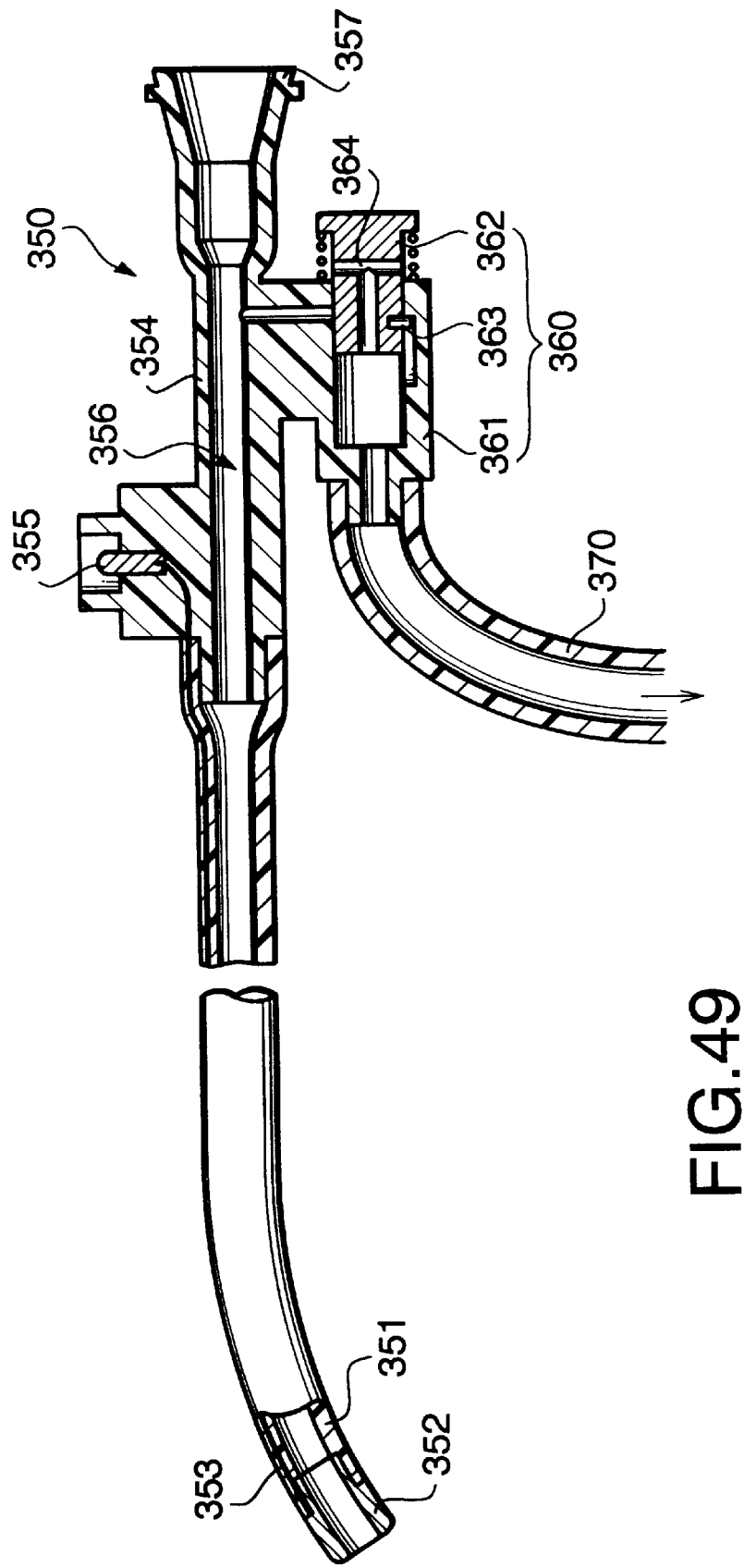
FIG. 49 is a sectional view of a cautery of a second modification of the seventh embodiment.
Figure 50:
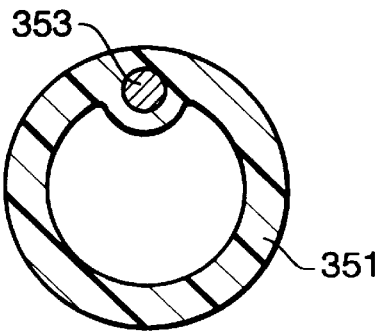
FIG. 50 is a sectional view of a tube of the cautery of FIG. 49.

FIGS. 49 and 50 are a sectional view and a front view showing the second modification of the seventh embodiment. As shown in FIG. 49, a suction tube 351 of this second modification is so constituted that a lead wire 353 is provided in a sheath of the suction tube 351. As shown in FIG. 50, the lead wire 353 is embedded in the sheath of the suction tube 351.

As shown in FIG. 49, a proximal end of the suction tube 351 is connected to a connector 354. The connector 354 has a through hole 356 connected to the suction tube 351 and an insertion port 357 for inserting a instrument (such as a forceps, an injector, a snare or the like) into the suction tube 351. The connector 354 is connected to a connection tube 370 connected to a not-shown suction apparatus. The connector 354 is further provided with a bulb unit 360. The bulb unit 360 includes a cylinder 361 provided in a path between the through hole 356 and the connection tube 370. A spring-loaded piston 362 is slidably provided in the cylinder 361. A connection hole 364 is formed in the piston 362. When the piston 362 is pressed, the connection hole 364 is moved to a position where the connection hole 364 connects the through hole 356 and the connection tube 370. When the piston 362 is not pressed, the piston 362 is retracted (due to the force of the spring), so that the through hole 356 and the connection tube 370 are not connected. Thus, the operator can easily control the suction via the suction tube 351 with a finger.

With such an arrangement, since the cable 353 does not exist in the suction tube 351, the suction tube 351 can be used for inserting an instrument such as a forceps, an injector or the like. Thus, it is possible to use both of the instrument and the electrode 352 at the same time.

Figure 51:
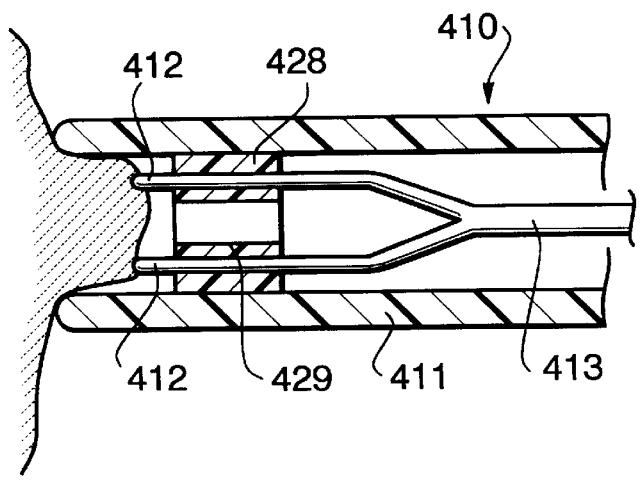
FIG. 51 is a sectional view of a cautery of a third modification of the seventh embodiment.

FIG. 51 is a sectional view showing the third modification of the seventh embodiment. In this modification, two electrode pins 412 are provided to the tip of a suction tube 411. The electrode pins 412 are connected to a lead wire 413 provided in the suction tube 411. In order to support the electrode pins 412, a support member 428 (made of insulation material) is provided at the distal end of the suction tube 411. The supporting member 428 is provided with a through hole 429 so that fluid can flow into the suction tube 411 therethrough.

Figure 52:
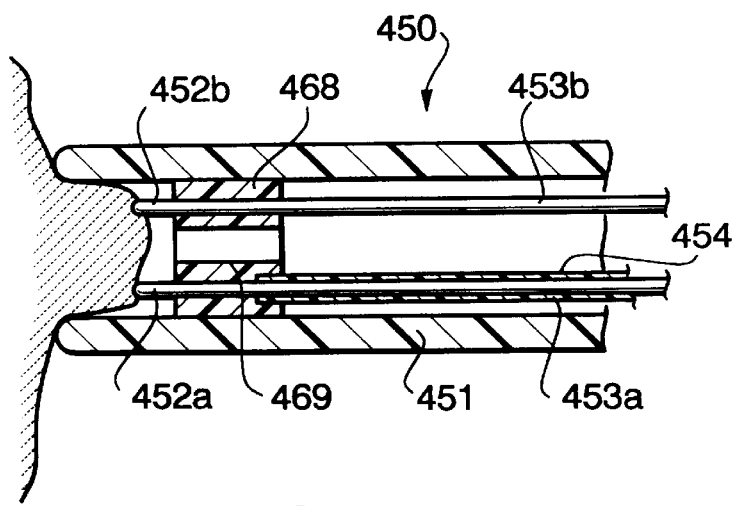
FIG. 52 is a sectional view of a cautery of fourth modification of the seventh embodiment.

FIG. 52 is a sectional view showing the fourth modification of the seventh embodiment. In this modification, two electrode pins 452a and 452b are provided to the tip of a suction tube 451. The electrode pins 452a and 452b are respectively connected to lead wires 453a and 453b provided through the suction tube 451. The lead wires 453a and 453b are connected to a not-shown power source. Plus voltage is applied to the electrode pin 452a and minus voltage is applied to the electrode pin 452b. In order to support the electrode pins 452a and 452b, a support member 468 (made of insulation material) is provided at the distal end of the suction tube 451. In order to separate the electrode pins 452a and 452b from each other, one electrode pin 452 is covered by an insulation cover 454. The supporting member 468 is provided with a through hole 469 so that fluid can flow into the suction tube 451 therethrough.

Although the structure and operation of an electric cautery is described herein with respect to the preferred embodiments, many modifications and changes can be made without departing from the spirit and scope of the invention.

The present disclosure relates to subject matters contained in Japanese Patent Application Nos. HEI 09-147756, HEI 09-147757 and HEI 09-147758 filed on Jun. 5, 1997, and Japanese Patent Application No. HEI 09-163580 filed on Jun. 20, 1997, which are expressly incorporated herein by reference in their entirety.

What is claimed is:

1. An electric cautery used with an endoscope,
said endoscope comprising an elongated insertion part to be inserted into a human body cavity, said insertion part having an image observing optical system at a distal end of said insertion part and at least one channel that opens at said distal end of said insertion part, said channel enabling suction,
said electric cautery comprising:
a hood mounted to said distal end of said insertion part;
at least one electrode provided to at least one of an inner surface and an end surface of said hood;
at least one cable which supplies electricity to said electrode, said cable extending in said channel;
said hood including a protrusion which inwardly protrudes from an inner surface of said hood, said cable and said electrode being electrically connected with each other at said protrusion.

2. An electric cautery used with an endoscope,
said endoscope comprising an elongated insertion part to be inserted into a human body cavity, said insertion part having an image observing optical system at a distal end of said insertion part and at least one channel that opens at said distal end of said insertion part, said channel enabling suction,
said electric cautery comprising:
a hood mounted to said distal end of said insertion part, said hood including a protrusion which inwardly protrudes from an inner surface of said hood;
at least one electrode provided to an outer surface of said hood;
at least one cable which supplies electricity to said electrode, said cable extending in said channel, said cable including a lead wire and a sheath covering said lead wire;
wherein said opening of said channel and said protrusion are overlapped with each other in a direction of the axis of said insertion part and said lead wire extends through said protrusion to said electrode.

3. An electric cautery used with an endoscope, said endoscope comprising an elongated insertion part to be inserted into a human body cavity, said insertion part having at least one channel,
said electric cautery comprising:
a tube inserted through said channel, said tube enabling suction;
at least one electrode provided to a tip of the tube, said electrode comprising a plurality of pins located in a hollow portion of said tube;
at least one cable which supplies electricity to said electrode, said cable extending through said tube.

4. The electric cautery according to claim 3, wherein said electrode extends in a hollow portion of said tube.

5. The electric cautery according to claim 3, wherein said electrode is provided to an inner surface of said tip of the tube.

6. The electric cautery according to claim 3, wherein said electrode is embedded in a sheath of said tube.

7. The electric cautery according to claim 3, wherein voltages of same polarity are applied to said plurality of pins.

8. The electric cautery according to claim 3, wherein voltages of reversed polarity are applied to said plurality of pins.

9. The electric cautery according to claim 3, further comprising a connector to which a proximal end of said tube is provided,
wherein said connector is connected to a suction apparatus.

10. The electric cautery according to claim 9, wherein said connector is provided with a control bulb that is used to control a suction through said tube.

11. The electric cautery according to claim 9, wherein a hole is formed on said connector,
a suction is enabled when an operator shields said opening of said connector.

12. An electric cautery used with an endoscope, said endoscope comprising an elongated insertion part to be inserted into a human body cavity, said insertion part having at least one channel that opens at a distal end of said insertion part, said channel enabling suction, said electric cautery comprising:
- a hood mounted to said distal end of said insertion part;
- at least one electrode provided to at least one of an inner surface and an end surface of said hood;
- at least one cable which supplies electricity to said electrode, said cable extending in said channel; and
- said hood including a protrusion which inwardly protrudes from an inner surface of said hood, said cable and said electrode being electrically connected with each other at said protrusion.

13. The electric cautery according to claim 12, said opening of said channel and said protrusion are overlapped with each other in a direction of axis of said insertion part.

14. The electric cautery according to claim 13, wherein a gap is provided between said protrusion and said opening of said channel.

15. The electric cautery according to claim 12, wherein said electrode partially extends in said protrusion.

16. An electric cautery used with an endoscope, said endoscope comprising an elongated insertion part to be inserted into a human body cavity, said insertion part having at least one channel that opens at a distal end of said insertion part, said channel enabling suction, said electric cautery comprising:
- a hood mounted to said distal end of said insertion part, said hood including a protrusion which inwardly protrudes from an inner surface of said hood,
- wherein said opening of said channel and said protrusion are overlapped with each other in a direction of axis of said insertion part;
- at least one electrode provided to an outer surface of said hood;
- at least one cable which supplies electricity to said electrode, said cable extending in said channel, said cable including a lead wire and a sheath covering said lead wire, wherein said lead wire extends through said protrusion to said electrode.

* * * * *